United States Patent
Spohn et al.

(10) Patent No.: US 10,137,294 B2
(45) Date of Patent: *Nov. 27, 2018

(54) FLOW BASED PRESSURE ISOLATION AND FLUID DELIVERY SYSTEM INCLUDING FLOW BASED PRESSURE ISOLATION AND FLOW INITIATING MECHANISM

(71) Applicant: BAYER HEALTHCARE LLC, Whippany, NJ (US)

(72) Inventors: Michael A. Spohn, Fenelton, PA (US); John A. Haury, Sewickley, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,153

(22) Filed: Dec. 20, 2016

(65) Prior Publication Data
US 2017/0100577 A1    Apr. 13, 2017

Related U.S. Application Data

(60) Continuation of application No. 14/579,139, filed on Dec. 22, 2014, now Pat. No. 9,526,829, which is a
(Continued)

(51) Int. Cl.
*A61M 5/175* (2006.01)
*A61M 39/24* (2006.01)
(Continued)

(52) U.S. Cl.
CPC ......... *A61M 39/24* (2013.01); *A61B 5/02141* (2013.01); *A61M 5/007* (2013.01);
(Continued)

(58) Field of Classification Search
CPC ............ A61B 5/0215; A61B 5/02141; A61M 2005/1403; A61M 2039/2433;
(Continued)

(56) References Cited

U.S. PATENT DOCUMENTS 1,832,266 A    11/1931  Thomas
2,191,990 A    2/1940   Jordan
(Continued)

FOREIGN PATENT DOCUMENTS

FR    2848859 A1    6/2004
JP    H0630905 A    2/1994
(Continued)

OTHER PUBLICATIONS

International Search Report for Corresponding International patent Application Publication PCT/US07/84403, dated Jun. 5, 2008.

*Primary Examiner* — William McCalister
(74) *Attorney, Agent, or Firm* — Joseph L. Kent; David Schramm; James R. Stevenson

(57) ABSTRACT

A method for protecting a pressure transducer from fluid pressure damage using a pressure isolation mechanism is disclosed. The method includes associating the pressure transducer with an isolation port of the pressure isolation mechanism, placing a pressurizing device for delivering fluid under pressure in fluid connection with an inlet port of the pressure isolation mechanism, and actuating the pressurizing device to cause fluid flow in the inlet port such that a free floating, fluid flow responsive valve member positioned in an internal cavity of the pressure isolation mechanism engages a seal seat therein to attain a closed position, preventing fluid flow between the inlet port and the isolation port and thus prevent overpressure in the isolation port. Hemodynamic pressure signals read with the pressure transducer may be transmitted at least in part through a body of the valve member, or a portion thereof, when in the closed position.

18 Claims, 30 Drawing Sheets

Related U.S. Application Data continuation of application No. 13/595,712, filed on Aug. 27, 2012, now Pat. No. 8,919,384, which is a continuation of application No. 12/563,463, filed on Sep. 21, 2009, now Pat. No. 8,251,092, which is a division of application No. 11/931,594, filed on Oct. 31, 2007, now Pat. No. 7,610,936, which is a continuation-in-part of application No. 11/615,371, filed on Dec. 22, 2006, now abandoned.

(51) Int. Cl.
| | | |
|---|---|---|
| A61M 5/00 | (2006.01) | |
| A61M 5/142 | (2006.01) | |
| A61B 5/021 | (2006.01) | |
| A61M 5/145 | (2006.01) | |
| A61M 5/172 | (2006.01) | |
| A61M 5/168 | (2006.01) | |
| A61M 39/22 | (2006.01) | |
| A61B 5/0215 | (2006.01) | |

(52) U.S. Cl.
CPC ........ *A61M 5/142* (2013.01); *A61M 5/14546* (2013.01); *A61M 5/16881* (2013.01); *A61M 5/172* (2013.01); *A61B 5/0215* (2013.01); *A61M 2039/229* (2013.01); *A61M 2039/248* (2013.01); *Y10T 137/0352* (2015.04); *Y10T 137/7758* (2015.04); *Y10T 137/7871* (2015.04); *Y10T 137/7915* (2015.04); *Y10T 137/85978* (2015.04); *Y10T 137/87829* (2015.04)

(58) Field of Classification Search
CPC .. A61M 2039/2453; A61M 2039/2473; A61M 2205/3362; A61M 2205/3306; A61M 2205/581; A61M 2205/583; A61M 39/24; A61M 5/007; A61M 5/1408; A61M 5/142; A61M 5/14546; A61M 5/16827; A61M 5/16831; A61M 5/1684; A61M 5/16881; A61M 5/365; A61M 2039/229; A61M 2039/248; A61M 5/172365; Y10T 137/0352; Y10T 137/7758; Y10T 137/7871; Y10T 137/7915; Y10T 137/85978; Y10T 137/87829
USPC .. 137/516.25, 516.27, 519, 485, 877, 519.5; 600/485, 486, 487, 488; 604/140
See application file for complete search history.

(56) References Cited

U.S. PATENT DOCUMENTS

| | | | |
|---|---|---|---|
| 2,202,123 A | 5/1940 | Strode |
| 2,223,944 A | 12/1940 | Roy |
| 2,415,258 A | 2/1947 | Parker et al. |
| 2,702,547 A | 2/1955 | Glass |
| 2,729,228 A | 1/1956 | Stevenson |
| 3,207,179 A | 9/1965 | Klagues |
| 3,565,056 A | 2/1971 | Statham |
| 3,633,605 A | 1/1972 | Smith |
| 3,645,139 A | 2/1972 | Zavoda |
| 3,675,891 A | 7/1972 | Reynolds et al. |
| 3,713,341 A | 1/1973 | Madsen et al. |
| 3,831,629 A | 8/1974 | Mackal et al. |
| 3,859,985 A | 1/1975 | Eckhart |
| 3,863,504 A | 2/1975 | Borsanyi |
| 3,865,100 A | 2/1975 | Kanai et al. |
| 4,005,219 A | 1/1977 | Buckle et al. |
| 4,005,710 A | 2/1977 | Zeddies et al. |
| 4,077,882 A | 3/1978 | Gangemi |
| 4,080,967 A | 3/1978 | O'Leary |
| 4,094,318 A | 6/1978 | Burke et al. |
| 4,109,535 A | 8/1978 | Reed et al. |
| 4,226,124 A | 10/1980 | Kersten |
| 4,243,031 A | 1/1981 | Genese |
| 4,314,480 A | 2/1982 | Becker |
| 4,335,729 A | 6/1982 | Reynolds et al. |
| 4,337,770 A | 7/1982 | Young et al. |
| 4,341,224 A | 7/1982 | Stevens |
| 4,351,332 A | 9/1982 | Whitney |
| 4,392,847 A | 7/1983 | Whitney et al. |
| 4,414,999 A | 11/1983 | Basta |
| 4,415,003 A | 11/1983 | Paradis et al. |
| 4,428,383 A | 1/1984 | Devroom |
| 4,431,009 A | 2/1984 | Marino, Jr. et al. |
| 4,444,198 A | 4/1984 | Petre |
| 4,444,219 A | 4/1984 | Hollenstein |
| 4,464,172 A | 8/1984 | Lichtenstein |
| 4,509,946 A | 4/1985 | McFarlane |
| 4,516,595 A | 5/1985 | Acomb |
| 4,517,844 A | 5/1985 | Powell |
| 4,624,662 A | 11/1986 | Le |
| 4,677,980 A | 7/1987 | Reilly et al. |
| 4,683,916 A | 8/1987 | Raines |
| 4,697,617 A | 10/1987 | Bourke et al. |
| 4,712,583 A | 12/1987 | Pelmulder et al. |
| 4,779,625 A | 10/1988 | Cole |
| 4,838,856 A | 6/1989 | Mulreany et al. |
| 4,858,127 A | 8/1989 | Kron et al. |
| 4,890,640 A | 1/1990 | King, Sr. |
| 4,960,127 A | 10/1990 | Noce et al. |
| 5,002,528 A | 3/1991 | Palestrant |
| 5,004,079 A | 4/1991 | Ivers et al. |
| 5,007,904 A | 4/1991 | Densmore et al. |
| 5,057,081 A | 10/1991 | Sunderland et al. |
| 5,076,280 A | 12/1991 | Moriuchi et al. |
| 5,106,379 A | 4/1992 | Leap |
| 5,120,313 A | 6/1992 | Elftman |
| 5,148,811 A | 9/1992 | Messinger |
| 5,237,999 A | 8/1993 | Von Berg |
| 5,241,986 A | 9/1993 | Yie |
| 5,273,047 A | 12/1993 | Tripp et al. |
| 5,300,031 A | 4/1994 | Neer et al. |
| 5,336,051 A | 8/1994 | Tamari |
| 5,383,858 A | 1/1995 | Reilly et al. |
| 5,423,751 A | 6/1995 | Harrison et al. |
| 5,429,611 A | 7/1995 | Rait |
| 5,433,712 A | 7/1995 | Stiles et al. |
| 5,460,609 A | 10/1995 | O'Donnell |
| 5,515,851 A | 5/1996 | Goldstein |
| 5,535,785 A | 7/1996 | Werge et al. |
| 5,554,113 A | 9/1996 | Novak et al. |
| 5,569,208 A | 10/1996 | Woelpper et al. |
| 5,573,515 A | 11/1996 | Wilson et al. |
| 5,575,767 A | 11/1996 | Stevens |
| 5,584,671 A | 12/1996 | Schweitzer, Jr. et al. |
| 5,593,385 A | 1/1997 | Harrison et al. |
| 5,692,539 A | 12/1997 | Pickl, Jr. |
| 5,727,594 A | 3/1998 | Choksi |
| 5,770,675 A | 6/1998 | Kim et al. |
| 5,775,671 A | 7/1998 | Cote, Sr. |
| 5,779,675 A | 7/1998 | Reilly et al. |
| 5,800,397 A | 9/1998 | Wilson et al. |
| 5,840,026 A | 11/1998 | Uber, III et al. |
| 5,873,861 A | 2/1999 | Hitchins et al. |
| 5,916,165 A | 6/1999 | Duchon et al. |
| 5,938,639 A | 8/1999 | Reilly et al. |
| 5,947,935 A | 9/1999 | Rhinehart et al. |
| 5,992,462 A | 11/1999 | Atkinson et al. |
| 6,029,076 A | 2/2000 | Fiddian-Greene et al. |
| 6,089,272 A | 7/2000 | Brand et al. |
| 6,096,011 A | 8/2000 | Trombley, III et al. |
| 6,099,502 A | 8/2000 | Duchon et al. |
| 6,221,045 B1 | 4/2001 | Duchon et al. |
| 6,336,913 B1 | 1/2002 | Spohn et al. |
| 6,344,030 B1 | 2/2002 | Duchon et al. |
| 6,346,084 B1 | 2/2002 | Schnell et al. |
| 6,390,120 B1 | 5/2002 | Guala |
| 6,390,130 B1 | 5/2002 | Guala |
| 6,471,674 B1 | 10/2002 | Emig et al. |
| 6,475,192 B1 | 11/2002 | Reilly et al. |

(56) References Cited

U.S. PATENT DOCUMENTS

| | | |
|---|---|---|
| 6,536,278 B1 | 3/2003 | Scagliarini |
| 6,595,957 B1 | 7/2003 | Griffiths et al. |
| 6,622,752 B2 | 9/2003 | Kushida et al. |
| 6,626,862 B1 | 9/2003 | Duchon et al. |
| 6,649,046 B2 | 11/2003 | Chevallet |
| 6,656,157 B1 | 12/2003 | Duchon et al. |
| 6,811,139 B2 | 11/2004 | Hishikawa |
| 6,866,039 B1 | 3/2005 | Wright et al. |
| 6,866,654 B2 | 3/2005 | Callan et al. |
| 6,896,002 B2 | 5/2005 | Hart et al. |
| 6,929,619 B2 | 8/2005 | Fago et al. |
| 6,945,959 B2 | 9/2005 | Duchon et al. |
| 6,986,753 B2 | 1/2006 | Bui |
| 6,988,510 B2 | 1/2006 | Enerson |
| 7,014,624 B2 | 3/2006 | Meythaler et al. |
| 7,094,216 B2 | 8/2006 | Trombley et al. |
| 7,153,288 B2 | 12/2006 | Duchon et al. |
| 7,192,416 B1 | 3/2007 | Lazzaro et al. |
| 7,267,667 B2 | 9/2007 | Houde et al. |
| 7,302,960 B2 | 12/2007 | Patzer |
| 7,326,186 B2 | 2/2008 | Trombley et al. |
| 7,389,788 B2 | 6/2008 | Wilson et al. |
| 7,549,977 B2 | 6/2009 | Schriver et al. |
| 7,563,249 B2 | 7/2009 | Schriver et al. |
| 7,610,936 B2 | 11/2009 | Spohn et al. |
| 7,611,503 B2 | 11/2009 | Spohn et al. |
| 7,704,236 B2 | 4/2010 | Denolly |
| 8,251,092 B2 | 8/2012 | Spohn et al. |
| 8,919,384 B2 * | 12/2014 | Spohn .................. A61M 5/007 137/877 |
| 9,526,829 B2 * | 12/2016 | Spohn .................. A61M 5/007 |
| 2002/0143294 A1 | 10/2002 | Duchon et al. |
| 2003/0011135 A1 | 1/2003 | Meacham |
| 2003/0011136 A1 | 1/2003 | Ramirez et al. |
| 2003/0040723 A1 | 2/2003 | Hart et al. |
| 2003/0139706 A1 | 7/2003 | Gray |
| 2004/0122370 A1 | 6/2004 | Joyce et al. |
| 2004/0143212 A1 | 7/2004 | Trombley et al. |
| 2004/0158205 A1 | 8/2004 | Savage |
| 2004/0168530 A1 | 9/2004 | Adolfs et al. |
| 2004/0217315 A1 | 11/2004 | Doyle |
| 2004/0254533 A1 | 12/2004 | Schriver et al. |
| 2005/0104444 A1 | 5/2005 | Callan et al. |
| 2005/0194047 A1 | 9/2005 | Bausmith, III |
| 2005/0230575 A1 | 10/2005 | Zelenski et al. |
| 2005/0234407 A1 | 10/2005 | Spohn et al. |
| 2005/0234428 A1 | 10/2005 | Spohn et al. |
| 2006/0065873 A1 | 3/2006 | Doyle |
| 2006/0108555 A1 | 5/2006 | Kiehne |
| 2006/0149189 A1 | 7/2006 | Diamond et al. |
| 2006/0155248 A1 | 7/2006 | Hashimoto et al. |
| 2006/0178632 A1 | 8/2006 | Trombley, III |
| 2006/0180202 A1 | 8/2006 | Wilson et al. |
| 2007/0161970 A1 | 7/2007 | Spohn et al. |
| 2008/0086087 A1 | 4/2008 | Spohn et al. |
| 2008/0154214 A1 | 6/2008 | Spohn et al. |

FOREIGN PATENT DOCUMENTS

| | | |
|---|---|---|
| JP | H07100212 A | 4/1995 |
| WO | 9707841 A2 | 3/1997 |
| WO | 0010629 A1 | 3/2000 |
| WO | 0204049 A1 | 1/2002 |
| WO | 2007146586 A2 | 12/2007 |

* cited by examiner

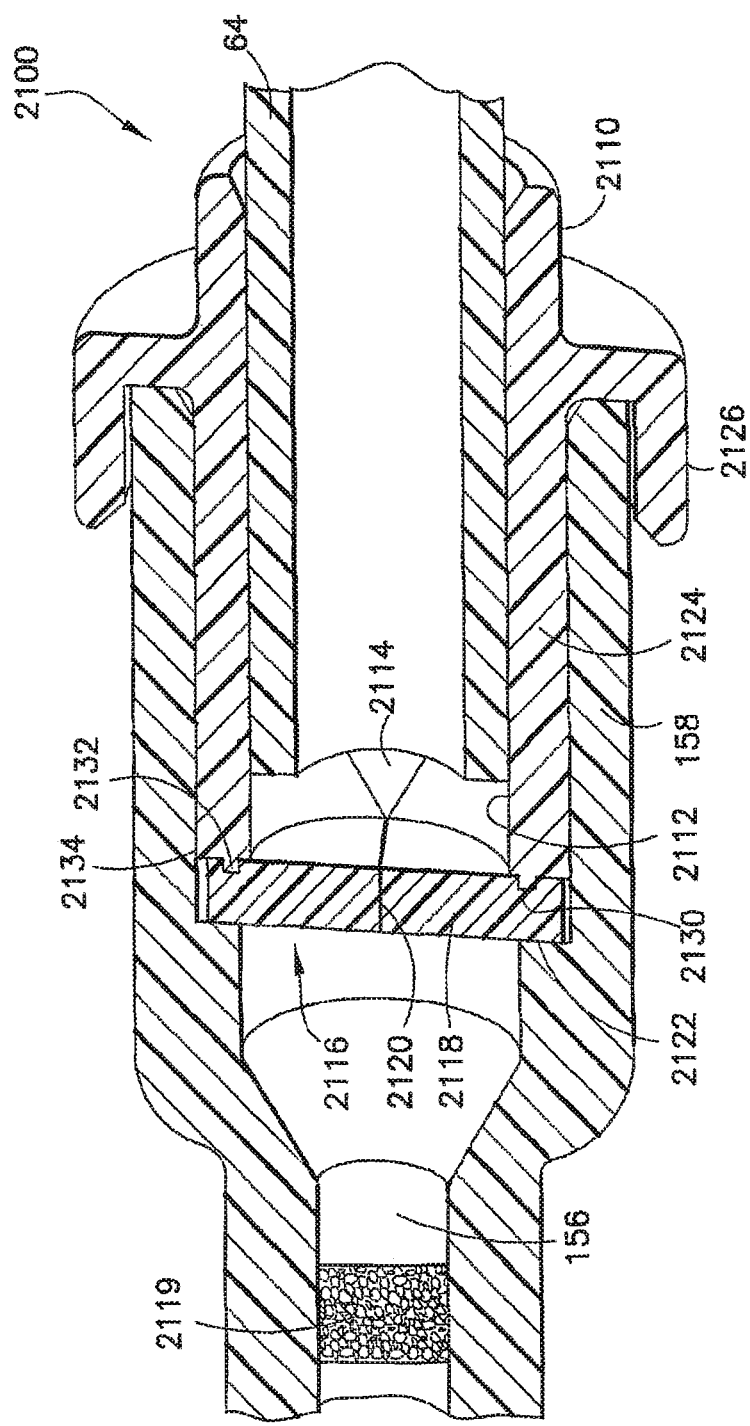

FLOW BASED PRESSURE ISOLATION AND FLUID DELIVERY SYSTEM INCLUDING FLOW BASED PRESSURE ISOLATION AND FLOW INITIATING MECHANISM

CROSS-REFERENCE TO RELATED APPLICATIONS

This application is a continuation application of application Ser. No. 14/579,139, filed Dec. 22, 2014, now U.S. Pat. No. 9,526,829, entitled "Flow Based Pressure Isolation and Fluid Delivery System Including Flow Based Pressure Isolation and Flow Initiating Mechanism;" which is a continuation application of application Ser. No. 13/595,712, filed Aug. 27, 2012, entitled "Flow Based Pressure Isolation and Fluid Delivery System Including Flow Based Pressure Isolation and Flow Initiating Mechanism," now U.S. Pat. No. 8,919,384; which is a continuation application of application Ser. No. 12/563,463, filed Sep. 21, 2009, entitled "Flow Based Pressure Isolation Mechanism for a Fluid Delivery System," now U.S. Pat. No. 8,251,092; which is a divisional application of application Ser. No. 11/931,594, filed Oct. 31, 2007, entitled "Flow Based Pressure Isolation Mechanism for a Fluid Delivery System," now U.S. Pat. No. 7,610,936; which is a continuation-in-part application of application Ser. No. 11/615,371, filed Dec. 22, 2006, entitled "Flow Based Pressure Isolation and Fluid Delivery System Including Flow Based Pressure Isolation," the disclosures of each of which are incorporated in their entirety by this reference.

This application may contain subject matter that is related to that disclosed in the following applications: U.S. application Ser. No. 11/551,027, filed Oct. 19, 2006 entitled "Fluid Delivery System, Fluid Path Set, and Pressure Isolation Mechanism with Hemodynamic Pressure Dampening Correction" which is a continuation-in-part of U.S. application Ser. No. 11/004,670, filed Dec. 3, 2004, now U.S. Pat. No. 8,540,698, entitled "Fluid Delivery System Including a Fluid Path Set and a Check Valve Connector" which is a continuation-in-part of U.S. application Ser. No. 10/826,149, filed Apr. 16, 2004, now U.S. Pat. No. 7,611,503, entitled "Fluid Delivery System, Fluid Path Set, Sterile Connector and Improved Drip Chamber and Pressure Isolation Mechanism" which may contain subject matter that is related to that disclosed in the following applications: (1) U.S. application Ser. No. 10/818,748, filed on Apr. 6, 2004, now U.S. Pat. No. 7,326,186; (2) U.S. application Ser. No. 10/818,477, filed on Apr. 5, 2004, now U.S. Pat. No. 7,563,249; (3) U.S. application Ser. No. 10/326,582, filed on Dec. 20, 2002, now U.S. Pat. No. 7,549,977; (4) U.S. application Ser. No. 10/237,139, filed on Sep. 6, 2002, now U.S. Pat. No. 6,866,654; and (5) U.S. application Ser. No. 09/982,518, filed on Oct. 18, 2001, now U.S. Pat. No. 7,094,216; the disclosures of all the foregoing applications are incorporated herein by reference.

BACKGROUND OF THE INVENTION

Field of the Invention

This invention is generally directed to the delivery of fluids in medical procedures and, more particularly, to apparatus, systems, and methods of protecting pressure transducers used to obtain physiological pressure measurements during fluid delivery procedures.

Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media (often referred to simply as "contrast"), have been developed for use in procedures such as angiography, computed tomography, ultrasound, and NMR/MRI. In general, these powered injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Automation of angiographic procedures using powered injectors is discussed, for example, in U.S. Pat. Nos. 5,460,609; 5,573,515; and 5,800,397.

The pressure transducers used with automatic contrast injection mechanisms and manual contrast injection mechanisms used to conduct fluid injection procedures such as angiographic and like procedures are extremely sensitive to even moderate pressures generated during activation of the syringe, so the operator must typically close a valve to isolate the pressure transducer from the fluid path when the syringe is activated to prevent damage to the pressure transducer. Specifically, many pressure transducers can be damaged if they are subjected to pressures as low as about 75 psi. Because even a hand-held syringe can generate pressures of 200 psi or more, the isolation of the pressure transducer is essential in order to avoid pressure transducer failure. While the syringe is not activated, the valve is usually open to monitor patient blood pressure.

In one known arrangement, the pressure transducer and contrast injection mechanism are connected to the catheter through a manifold. The manifold includes a valve which enables the injector operator to isolate the pressure transducer during the injection of the contrast solution. This valve, typically a stopcock, is used to isolate the pressure transducer to prevent damage thereto. Specifically, a stopcock configuration is provided which either allows the pressure transducer to be in fluid communication with the catheter or the contrast injection mechanism to be in fluid communication with the catheter, but not both. Typically, the stopcock handle must be turned manually to switch between the two positions. Accordingly, this configuration provided by some currently available manifolds does not allow contrast injection to be made while the pressure transducer is in communication with the catheter.

One problem associated with the foregoing valve-manifold design is that the operator often forgets to turn the stopcock back to the position where the pressure transducer is in fluid communication with the catheter. As a result, the monitoring of the vessel or artery is interrupted for time periods longer than necessary. The monitoring of the vessel or artery pressure is important during almost any vascular procedure. Accordingly, when the operator fails to turn the stopcock handle, other members of the medical team must interrupt the operator and tell him or her to turn the pressure transducer back on which may cause an unnecessary distraction during a delicate medical procedure.

A well-established pressure transducer protection design includes, typically, a two-pieced housing formed from generally hemispherical members that form a "pressure dome" wherein a generally planar diaphragm or membrane is positioned. The diaphragm or membrane is centered within the housing and has a thickness that permits deflection within the housing in response to a pressure differential within the pressure dome. Thus, the diaphragm or membrane deflects or stretches in response to a pressure differential and this deflection is transmitted via a suitable pressure transmitting media in the pressure dome to the isolated pressure transducer. Examples of the foregoing diaphragm-type pressure transducer isolator design are disclosed in U.S. Pat. No. 4,314,480 to Becker; U.S. Pat. No. 4,226,124 to Kersten; U.S. Pat. No. 4,077,882 to Gangemi; and U.S. Pat. No. 3,863,504 to Borsanyi; U.S. Pat. No. 3,713,341 to Madsen et al.; and U.S. Pat. No. 3,645,139 to Zavoda, as examples. In the non-medical area, examples of pressure isolation devices for pressure gauges are disclosed in U.S. Pat. No. 3,207,179 to Klagues and U.S. Pat. No. 2,191,990 to Jordan.

U.S. Pat. No. 6,896,002 to Hart et al. discloses a pressure transducer protection device particularly adapted for angiographic fluid delivery systems. The pressure transducer protection device disclosed by this patent is in the form of a pressure activated valve for a three-way connection between a catheter, an injector, and a pressure transducer. The valve includes a body that has an inlet for connection to an injector, an outlet for connection to a catheter, and a secondary connection for connection to a pressure transducer. The body also includes a seal seat disposed between the secondary connection in both the inlet and the outlet. The body is flexibly connected to a plug seal. The plug seal is disposed between the seal seat in both the inlet and the outlet. The plug seal is movable between an open position spaced apart from the seal seat and biased towards the inlet and the outlet and a closed position against the seal seat thereby isolating the secondary connection from both the inlet and the outlet.

Another valve used for pressure transducer protection purposes is disclosed by U.S. Patent Application Publication No. 2006/0180202 to Wilson et al. This publication discloses an elastomeric valve having a valve body with three ports including a contrast inlet port, a saline inlet and pressure transducer port, and a patient or outlet port. The valve body houses a disc holder and a valve disc therein. The valve disc is molded of an elastomer, such as silicone rubber, with a slit in the center. The elastomeric disc is sandwiched between the valve body and disc holder and is affixed therebetween at the perimeter of the disc. Such affixation may be effected by entrapment, adhesion, mechanical or chemical welding. The elastomeric valve disclosed by this publication is responsive to pressure changes in the valve which act on the elastomeric disc.

Despite the contributions of Hart and Wilson et al., there is a general need for an improved pressure transducer protection device which can operate automatically to isolate a pressure transducer used to obtain physiological pressure measurements, particularly those pressure transducers used in potentially damaging fluid pressure environments such as angiography.

BRIEF SUMMARY

The flow-based pressure isolation techniques described herein for protection of a pressure transducer may take the form of a flow-based pressure isolation mechanism in one embodiment. In this embodiment, the flow-based pressure isolation mechanism comprises a housing body defining an inlet port, an isolation port, and an internal cavity. The housing body further defines a seal seat in the internal cavity between the inlet port and isolation port. A valve member is disposed in the internal cavity and is free floating in the internal cavity and adapted to engage the seal seat. The valve member has an open position permitting fluid communication between the inlet port and isolation port. The valve member is fluid flow responsive to fluid flow in the inlet port to engage the seal seat and attain a closed position preventing fluid flow between the inlet port and isolation port. A pressure transducer is typically associated with the isolation port.

An optional flow initiating mechanism may be associated with the isolation port and is adapted to initiate flow around the valve member such that the valve member operates to a closed position substantially upon flow initiation. The flow initiating member may be disposed in a lumen in fluid communication with the isolation port. The flow initiating mechanism typically comprises a flow initiating member maintained in the lumen by a retainer. A filter may be disposed in a bore in the retainer. The bore is in fluid communication with the isolation port and the filter is generally adapted to prevent air from entering the internal cavity when wetted with fluid. In another variation, the housing body further defines a second seal seat radially outward and concentric to the first seal seat.

In one form, the valve member may comprise a disk member. The valve member may comprise a stiffening element associated with the disk member. In one form, the stiffening element may be cylindrical shaped. In other forms, the valve member may comprise a ball member. The disk member may be formed of compliant material. The compliant material is desirably selected to transmit hemodynamic pressure signals through the valve member to a pressure transducer associated with the isolation port.

One or both of the valve member and internal cavity may be shaped to permit fluid flow between the inlet port and isolation port in the open position and prevent fluid flow between the inlet port and isolation port in the closed position. Moreover, a volumetric capacitance element may be disposed in the internal cavity.

Another embodiment disclosed herein relates to a fluid delivery system that includes flow-based pressure isolation of a pressure transducer. Such a system comprises a pressurizing device for delivering a pressurized injection fluid, a low pressure fluid delivery system, and a pressure isolation mechanism adapted for fluid communication with the pressurizing device and low pressure fluid delivery system. The pressure isolation mechanism comprises a housing defining an inlet port, an isolation port, and an internal cavity. The housing defines a seal seat in the internal cavity between the inlet port and isolation port. A valve member is disposed in the internal cavity. The valve member is free floating in the internal cavity and is adapted to engage the seal seat. The valve member has an open position permitting fluid communication between the inlet port and isolation port, and is fluid flow responsive to fluid flow in the inlet port to engage the seal seat and attain a closed position preventing fluid flow between the inlet port and isolation port. The inlet port may be in fluid communication with the pressurizing device and low pressure fluid delivery system via a fitting.

In the fluid delivery system, an optional flow initiating mechanism may be associated with the isolation port and is adapted to initiate flow around the valve member such that the valve member operates to a closed position substantially upon flow initiation. The flow initiating member may be disposed in a lumen in fluid communication with the isolation port. The flow initiating mechanism typically comprises a flow initiating member maintained in the lumen by a retainer. A filter may be disposed in a bore in the retainer. The bore is in fluid communication with the isolation port and the filter is generally adapted to prevent air from entering the internal cavity when wetted with fluid. In another variation, the housing body further defines a second seal seat radially outward and concentric to the first seal seat.

The inlet port may be in fluid communication with the pressurizing device and the housing body and further define a low pressure fluid port connected to the low pressure fluid delivery system. The low pressure fluid port is in fluid communication with the isolation port and is isolated from the inlet port in the closed position of the valve member. A valve arrangement may be associated with the low pressure fluid port for regulating fluid flow through the low pressure fluid port. The valve arrangement in one form may comprise a disk valve defining one or more passageways regulating fluid flow through the low pressure fluid port.

In one form, the valve member for the pressure isolation mechanism associated with the fluid delivery system may comprise a disk member. In one form, the stiffening element may be cylindrical shaped. In other forms, the valve member may comprise a ball member. The disk member may be formed of compliant material. The compliant material is desirably selected to transmit hemodynamic pressure signals through the valve member to a pressure transducer associated with the isolation port.

One or both of the valve member and internal cavity may be shaped to permit fluid flow between the inlet port and isolation port in the open position and prevent fluid flow between the inlet port and isolation port in the closed position. Moreover, a volumetric capacitance element may be disposed in the internal cavity.

The protection of a pressure transducer may take the form of a method in another embodiment disclosed herein. The flow-based pressure isolation method protects a pressure transducer from fluid pressure damage using the pressure isolation mechanism summarized hereinabove. The pressure isolation mechanism comprises an inlet port, an isolation port, and an internal cavity wherein a free floating, fluid flow responsive valve member is disposed and adapted to engage a seal seat in the internal cavity. An optional flow initiating mechanism may be associated with the isolation port. The method generally comprises associating the pressure transducer with the isolation port; placing a pressurizing device for delivering fluid under pressure in fluid connection with the inlet port; actuating the pressurizing device to cause fluid flow in the inlet port such that the free floating, fluid flow responsive valve member engages the seal seat to attain a substantially closed position and prevent fluid flow between the inlet port and isolation port. In a variation of the foregoing method, upon actuation of the pressure device, the flow initiating mechanism may initiate flow around the valve member such that the valve member operates to the closed position substantially upon flow initiation.

The method may further comprise deactuating the pressurizing device and allowing the valve member to attain an open position disengaged from the seal seat permitting fluid communication between the inlet port and isolation port.

As part of the method hemodynamic pressure signals may be read with the pressure transducer, with the signals transmitted via the fluid communication between the inlet port and isolation port in the open position of the valve member. The hemodynamic pressure signals may even be read with the pressure transducer in the substantially closed position of the valve member by being transmitted at least in part through the body of the valve member, typically having at least a portion thereof formed on compliant material.

The pressure isolation mechanism may further comprise a low pressure fluid port connected to a low pressure fluid delivery system, the low pressure fluid port in fluid communication with the isolation port and isolated from the inlet port in the closed position of the valve member. The method may further comprise isolating the low pressure fluid delivery system from hemodynamic blood pressure signals with a valve arrangement in the low pressure fluid delivery port.

Further details and advantages will become clear upon reading the following detailed description in conjunction with the accompanying drawing figures, wherein like parts are identified with like reference numerals throughout.

BRIEF DESCRIPTION OF THE DRAWINGS

FIG. 21 is a partial cross-sectional view of the flow-based pressure isolation mechanism of FIG. 17 illustrating a valve arrangement adapted to provide hemodynamic pressure dampening correction.

DETAILED DESCRIPTION

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

Figure 1:
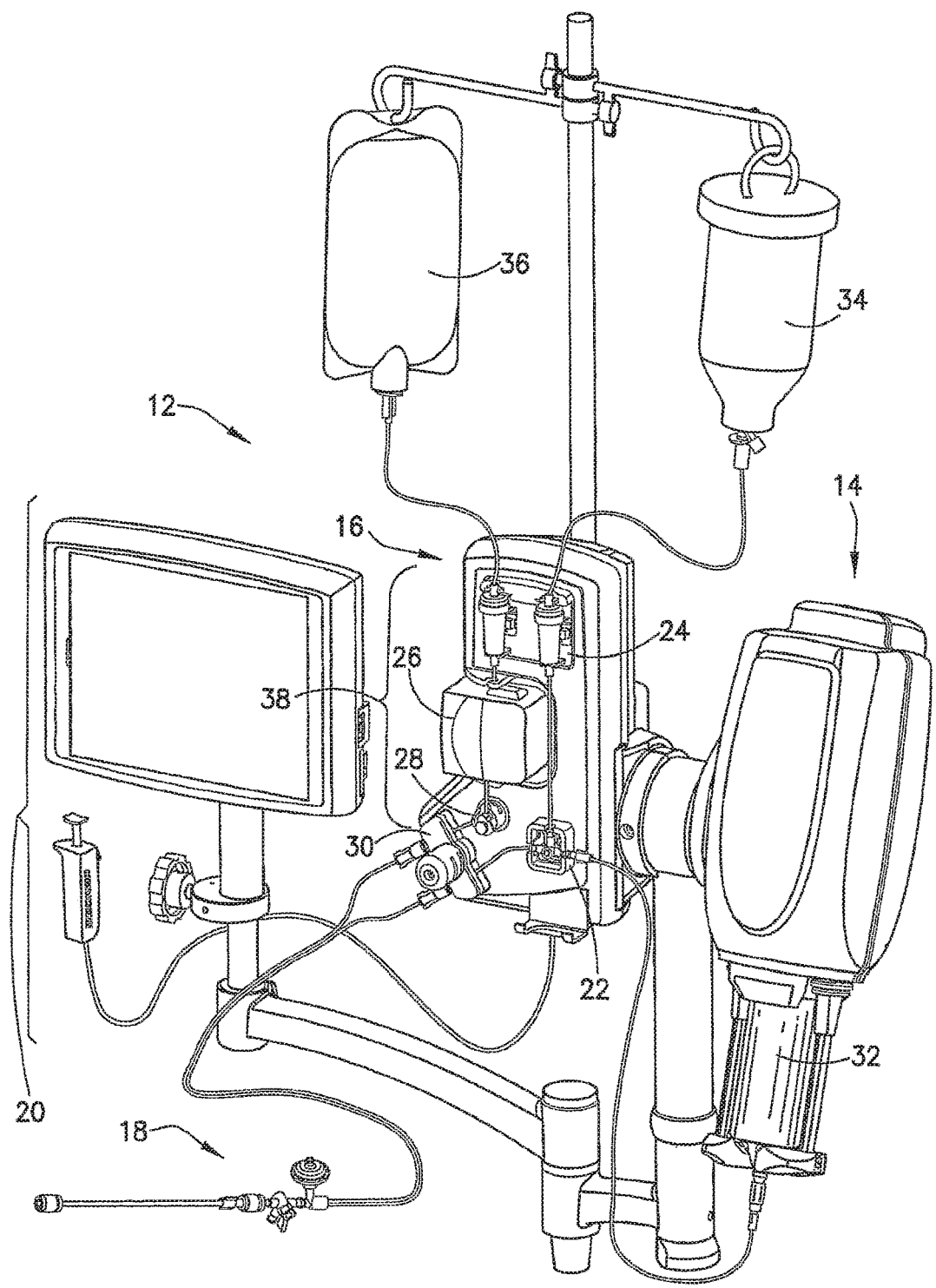
FIG. 1 is a perspective view of a fluid delivery system including a fluid path set that utilizes flow-based pressure isolation for the protection of a pressure transducer.

A fluid injector or delivery system 12 is illustrated generally in FIG. 1 and includes flow-based pressure isolation techniques for the protection of a pressure transducer P (FIG. 2A) used to take hemodynamic pressure readings during a fluid injection or delivery procedure. Fluid delivery system 12 includes, generally, a fluid injector 14 operatively associated with a fluid control module 16. The details of fluid injector 14 are set forth in U.S. patent application Ser. No. 10/818,477, now U.S. Pat. No. 7,563,249, the disclosure of which was incorporated herein by reference previously. Fluid injector 14 is adapted to support and actuate a fluid delivery syringe, as described herein in connection with FIG. 2B. Fluid control module 16 is associated with fluid injector 14 for controlling fluid flows delivered by the fluid injector 14. The details of fluid control module 16 are set forth in U.S. patent application Ser. No. 10/826,149, now U.S. Pat. No. 7,611,503, incorporated herein by reference previously. Fluid control module 16 is generally adapted to support and control a fluid path set 18 used to connect a syringe associated with fluid injector 14 to a catheter (not shown) to be associated with a patient. Fluid injector 14 and a syringe associated therewith serve as a pressurizing device for pressurizing fluid, such as contrast media ("contrast"), to be injected into a patient via the catheter. As an example, fluid injector 14 may be used as a vehicle to inject contrast at high fluid pressure into a blood vessel of a patient undergoing angiography. Additionally, fluid delivery system 12 includes a user-input control section or device 20 for interfacing with computer hardware/software (i.e., electronic memory) of fluid control module 16 and/or fluid injector 14, the details of which are identified in the foregoing Applications incorporated by reference. While the details of fluid control module 16 are set forth in detail in U.S. patent application Ser. No. 10/826,149, now U.S. Pat. No. 7,611,503, fluid control module 16 generally includes a housing unit supporting a valve actuator 22 for controlling a fluid control valve, such as a three-way stopcock, a fluid level sensing mechanism 24, a peristaltic pump 26, an automatic shut-off or pinch valve device 28, and an air detector assembly 30.

Figure 2A:
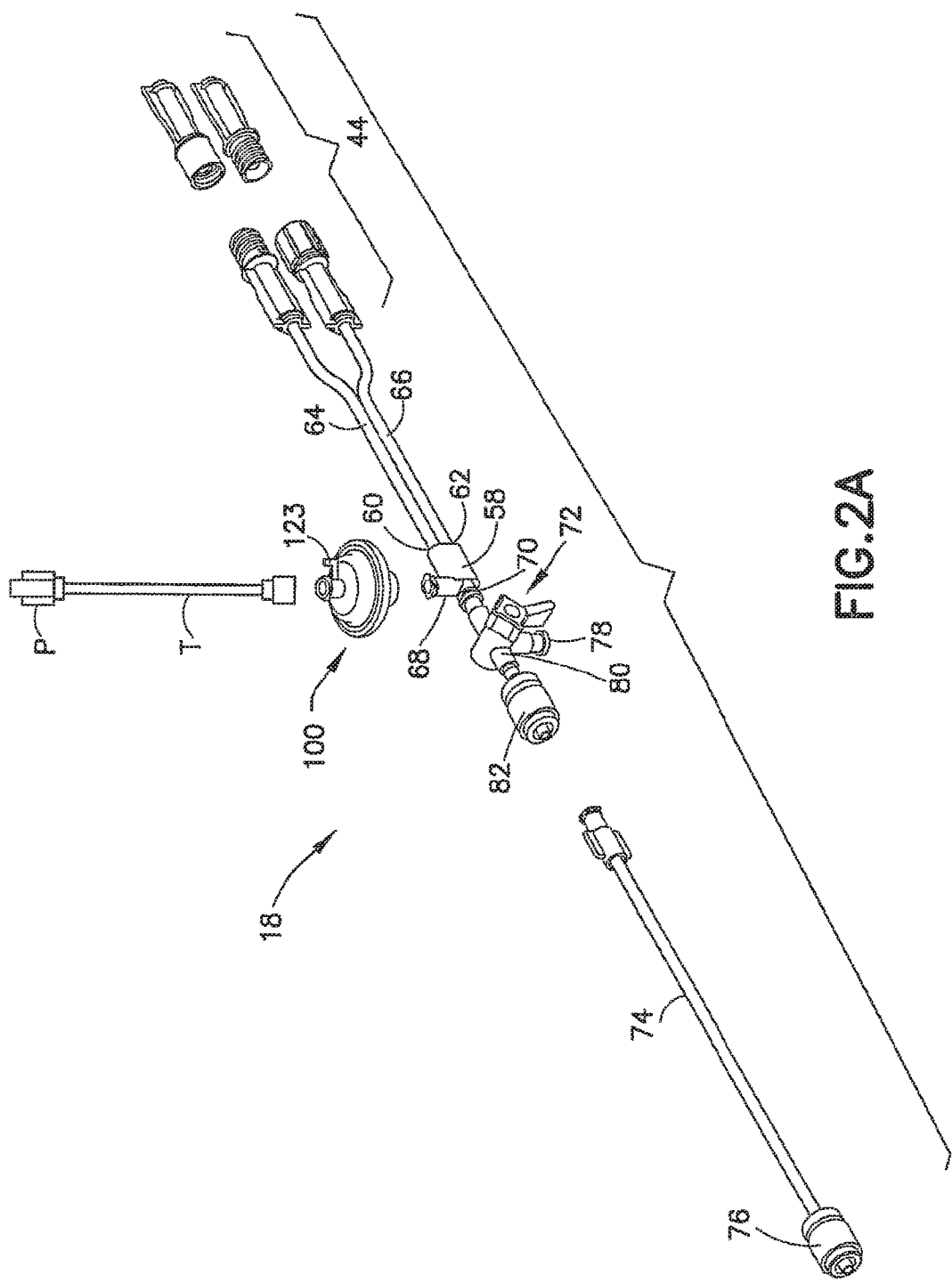
FIG. 2A is a perspective view of a portion of the fluid path set used in the fluid delivery system of FIG. 1 and which incorporates a flow-based pressure isolation mechanism.
Figure 2B:
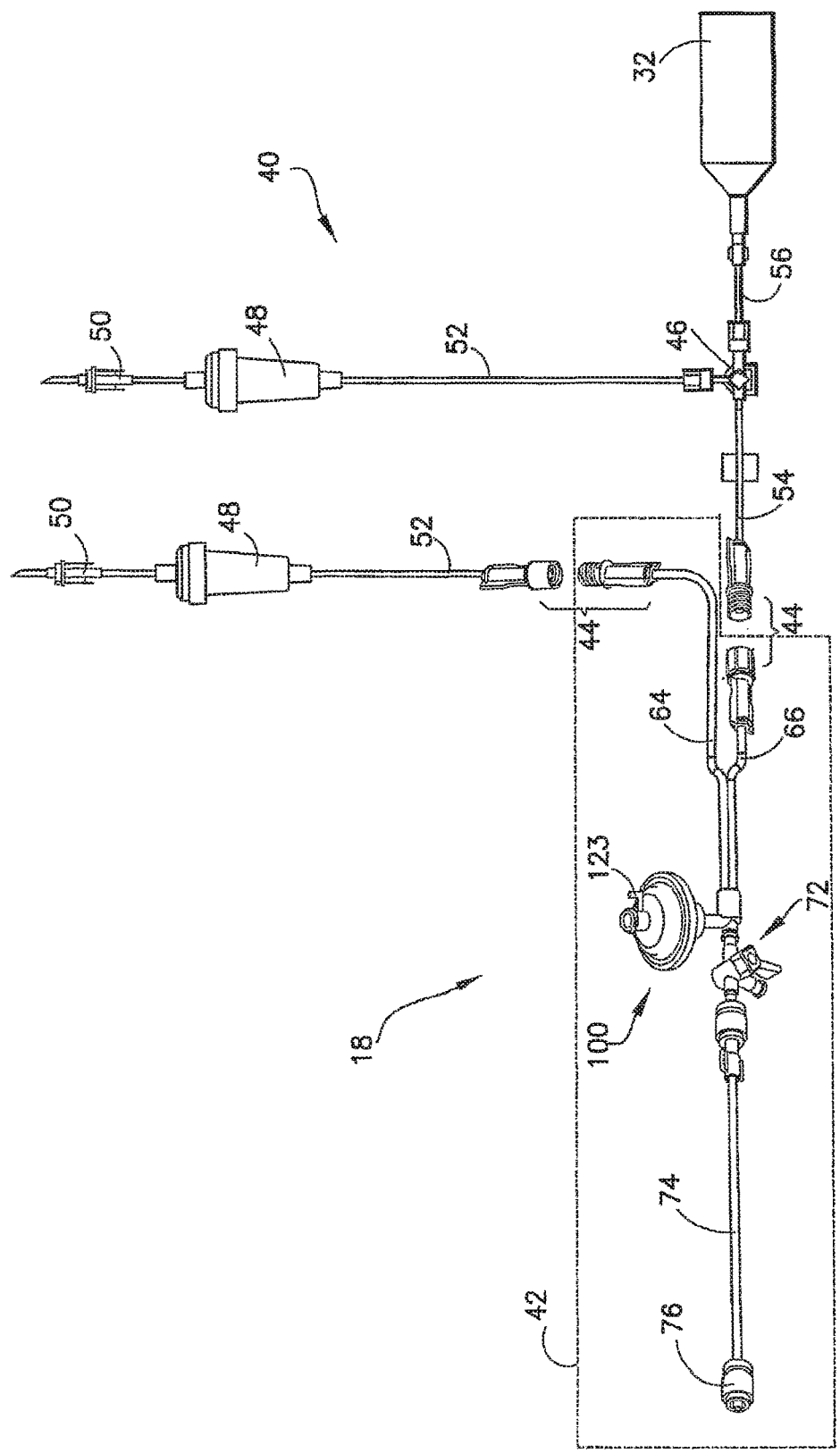
FIG. 2B is a side and partially perspective view of the complete fluid path set used in the fluid delivery system of FIG. 1.

Referring additionally to FIGS. 2A-2B, fluid control module 16 is generally adapted to support and control fluid flow through fluid path set 18 used to connect a syringe 32 associated with fluid injector 14 to a catheter (not shown) inserted in a patient. Fluid path set ("fluid path 18") may be considered to include syringe 32 that is associated with front-load fluid injector 14. Fluid path 18 is generally used to associate syringe 32 with a first or primary source of injection fluid 34, such as contrast, provided in a conventional medical container, which will be loaded into syringe 32 for a fluid injection procedure. First or primary fluid source 34 may be contrast in the case of angiographic or computed tomography procedures, as examples. Fluid path 18 is further adapted to associate syringe 32 with a secondary or additional source of fluid 36 also provided in a conventional medical container, which is to be supplied or delivered to the patient via the catheter. In a typical fluid delivery procedure, whether angiography or computed tomography, saline is often used as a secondary flushing fluid which is supplied to the patient between injections of contrast for clearing the catheter or clearing fluid path 18 of contrast, etc.

In a general fluid injection procedure involving fluid delivery system 12, fluid injector 14 is filled with fluid from primary fluid source 34 and delivers this fluid via fluid path 18 to the catheter and, ultimately, the patient. Fluid control module 16 generally controls or manages the delivery of the injection fluid through a control valve, such as a three-way stopcock, associated with fluid path 18 which is controlled or actuated by valve actuator 22 on the fluid control module 16. Fluid control module 16 is further adapted to deliver fluid from the secondary fluid source 36 under pressure via peristaltic pump 26 associated with the fluid control module 16. In a typical fluid injection procedure, valve actuator 22 actuates a valve, such as a three-way stopcock, associated with fluid path 18 which alternately permits fluid from the first or primary fluid source 34 to be loaded to syringe 32 associated with fluid injector 14 and then placed in a state to allow fluid communication or connection between syringe 32 and downstream portions of the fluid path 18 for delivering fluid such as contrast to the catheter connected to the fluid path 18. In a typical angiographic procedure as an example, fluid injector 14 may pressurize the contents of syringe 32 to pressures exceeding 1200 psi. Thus, fluid injector 14 and syringe 32 form a pressurizing device capable of providing contrast and like injection fluids to a patient under high pressure via fluid path 18 which is ultimately connected to an indwelling catheter inserted into a blood vessel of the patient. Peristaltic pump 26 and secondary fluid source 36 form a low pressure fluid delivery system 38 which provides a secondary injection fluid such as saline via the fluid path 18 to the patient and primarily for flushing the fluid path 18 and the catheter inserted in the patient, as indicated previously.

Fluid path 18 is generally comprised of a first section or portion 40 and a second section or portion 42. First section 40 is generally adapted to connect syringe 32 to the primary fluid source 34 and the second section 42, and to connect the second section 42 to the secondary fluid source 36. First section 40 may be used as a multi-patient section or set disposed of after a preset number of fluid injection procedures are accomplished with fluid delivery system 12. Thus, first section 40 may be used for a preset number of fluid injection procedures involving one or more patients and may then be discarded. Optionally and less desirably, first section 40 may be adapted to be re-sterilized for reuse. First section 40 is provided as a sterile set typically in a sterile package. Second section 42 is intended as a per-patient section or set which is disposed of after each fluid injection procedure involving fluid delivery system 12. First section 40 and second section 42 are placed in fluid communication by use of one or more connectors 44, the details of which are set forth in U.S. patent application Ser. No. 11/551,027 previously incorporated by reference.

First section 40 includes a multi-position valve 46 such as a three-way stopcock valve which is adapted to be automatically controlled or actuated by valve actuator 22 associated with fluid control module 16. In general, multi-position valve 46 may be actuated by valve actuator 22 to selectively isolate the syringe 32 and the primary fluid source 34 from the remainder of fluid path 18 and place the syringe 32 in fluid connection with the primary fluid source 34. This selectively allows fluid injector 14 to fill syringe 32 with fluid from primary fluid source 34, deliver fluid loaded into syringe 32 to fluid path 18 under pressure while isolating the primary fluid source 34, or isolate the syringe 32 and primary fluid source 34 from the remainder of the fluid path 18.

First section 40 includes intervening drip chambers 48 associated with the primary fluid source 34 and secondary fluid source 36. It is possible to replace drip chambers 48 with priming bulbs (not shown) in fluid path 18, if desired. Drip chambers 48 are adapted to be associated with the containers forming primary and secondary fluid sources 34, 36 with conventional spike members 50. Fluid level sensing mechanism 24 on fluid control module 16 is used to sense fluid levels in drip chambers 48 when fluid path 18 is associated with fluid injector 14 and fluid control module 16. Generally, operation of fluid delivery system 12 includes loading syringe 32 with fluid from the primary fluid source 34, which passes to the syringe 32 via the drip chamber 48 associated with the primary fluid source 34. Similarly, during operation of fluid delivery system 12 fluid, such as saline, from the secondary fluid source 36 is supplied to fluid path 18 via the drip chamber 48 associated with the secondary fluid source 36. Drip chambers 48 are generally adapted to permit fluid level sensors associated with fluid level sensing mechanism 24 to detect the level of fluid in the drip chambers 48, for example, by using optical or ultrasonic methods.

Respective output lines 52 made, for example, of conventional low pressure medical tubing, are associated with drip chambers 48 for connecting the drip chambers 48 to multi-position valve 46 and second section 42 of fluid path 18, respectively. An output line 54 from multi-position valve 46 connects the multi-position valve 46 and syringe 32 to second section 42 of fluid path 18 via connector 44. Due to the high injection pressures typically generated by fluid injector 14 during a fluid injection procedure such as angiography, output line 54 is desirably a high pressure medical tubing line. Additionally, a connecting tubing line 56 connecting multi-position valve 46 and syringe 32 is also desirably a high pressure medical tubing line to withstand these high fluid injection pressures.

A pressure isolation mechanism 100 is provided as part of fluid path 18 and the disposable second section 42 thereof in particular. Pressure isolation mechanism 100 serves several functions in fluid delivery system 12 but is primarily provided to connect the pressure transducer P to fluid path 18 so that hemodynamic blood pressure signal readings may be obtained during fluid delivery procedures involving fluid delivery system 12. In certain embodiments described herein (FIGS. 17-20 as an example), this mechanism may serve as a physical merge point for the primary and secondary injection fluid paths, such as contrast and saline, for delivery to a patient during a fluid injection or delivery procedure via a catheter. Due to the need to protect pressure transducer P from damaging fluid pressure, which can occur at fluid pressure as low as about 75 psi and higher as indicated previously, pressure isolation mechanism 100 includes internal valve structure that provides automatic overpressure protection for pressure transducer P during fluid delivery procedures, particularly those associated with the delivery of contrast at high pressure during angiographic procedures. Further details of pressure isolation mechanism 100 are provided hereinafter.

Pressure isolation mechanism 100 is typically associated with second section 42 of fluid path 18 via a Y-T fitting 58 having two input ports 60, 62 respectively connected to input lines 64, 66. Y-T fitting 58 in this embodiment and other embodiments discussed hereinafter serves as the merge point for the primary and secondary injection fluid paths, such as contrast and saline, for delivery to a patient via a catheter during a fluid injection or delivery procedure. Input lines 64, 66 comprise a first input line 64 associated with the low pressure fluid delivery system 38 generally and output line 52 connected to drip chamber 48 associated with the secondary fluid source 36 in particular, and a second input line 66 associated with the high pressure system or device comprised by syringe 32 and fluid injector 14. This high pressure side of the fluid path 18 is alternately placeable in fluid communication with output line 52 connected to the drip chamber 48 associated with the primary fluid source 34 as described previously to fill syringe 32 with primary injection fluid, typically contrast. Both first input line 64 and the upstream output line 52 associated with secondary fluid source 36 are desirably high pressure medical tubing lines to avoid any damage to the first input line 64 and upstream output line 52 from high backpressure through the Y-T fitting 58. However, with the addition of a check valve in input port 60 of Y-T fitting 58, conventional low pressure medical tubing may be used for first input line 64 and upstream output line 52. Alternatively, first input line 64 could be made of high pressure medical tubing line and upstream output line 52 made of low pressure medical tubing with the addition of a check valve associated with the connector 44 used to connect first input line 64 to upstream output line 52 to isolate output line 52 from high backpressure through Y-T fitting 58. Similarly, second input line 66 is desirably formed of high pressure medical tubing and connects second input port 62 with output line 54 connected to multi-position valve 46 and, thereby, syringe 32. While Y-T fitting 58 is a convenient device to merge the primary and secondary fluid paths its presence in fluid path 18 is only exemplary and other merging arrangements may be used in place of Y-T fitting 58 as evidenced by the arrangement illustrated in FIGS. 17-20.

Y-T fitting 58 further comprises a pressure transducer port 68 for associating the pressure isolation mechanism 100 with fitting 58, and an outlet port 70. A multi-position valve 72, such as three-way stopcock, is connected to outlet port 70 and may be used as a simple shut-off valve to isolate the catheter (not shown) from fluid path 18. A catheter connection line 74 terminating in a luer connector 76 is associated with multi-position valve 72. One of the ports of the multi-position valve 72 may be a waste port 78 and the remaining port comprises an outlet port 80 that is configured with a luer connector 82 for associating catheter connection line 74 to multi-position valve 72 and, thus, fluid path 18.

Figure 3:
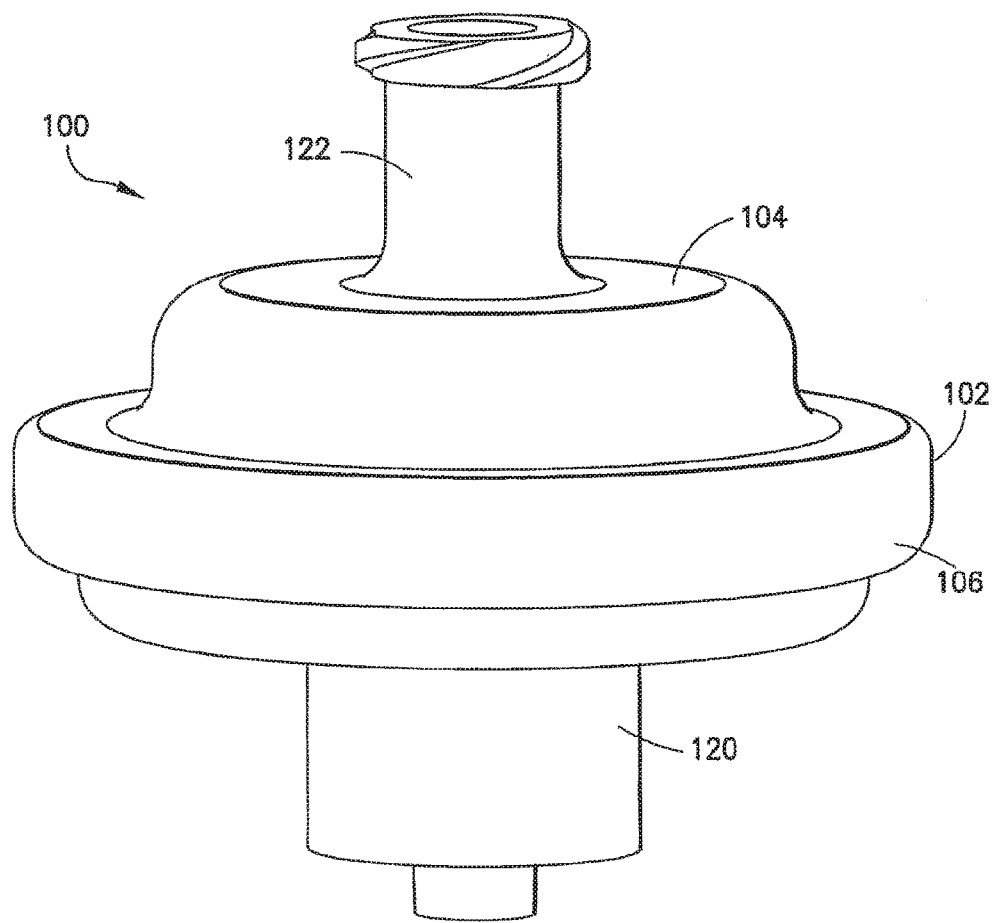
FIG. 3 is a perspective view of a first embodiment of the flow-based pressure isolation mechanism incorporating a flow-responsive valve member in the form of a flow-responsive disk valve member.
Figure 4:
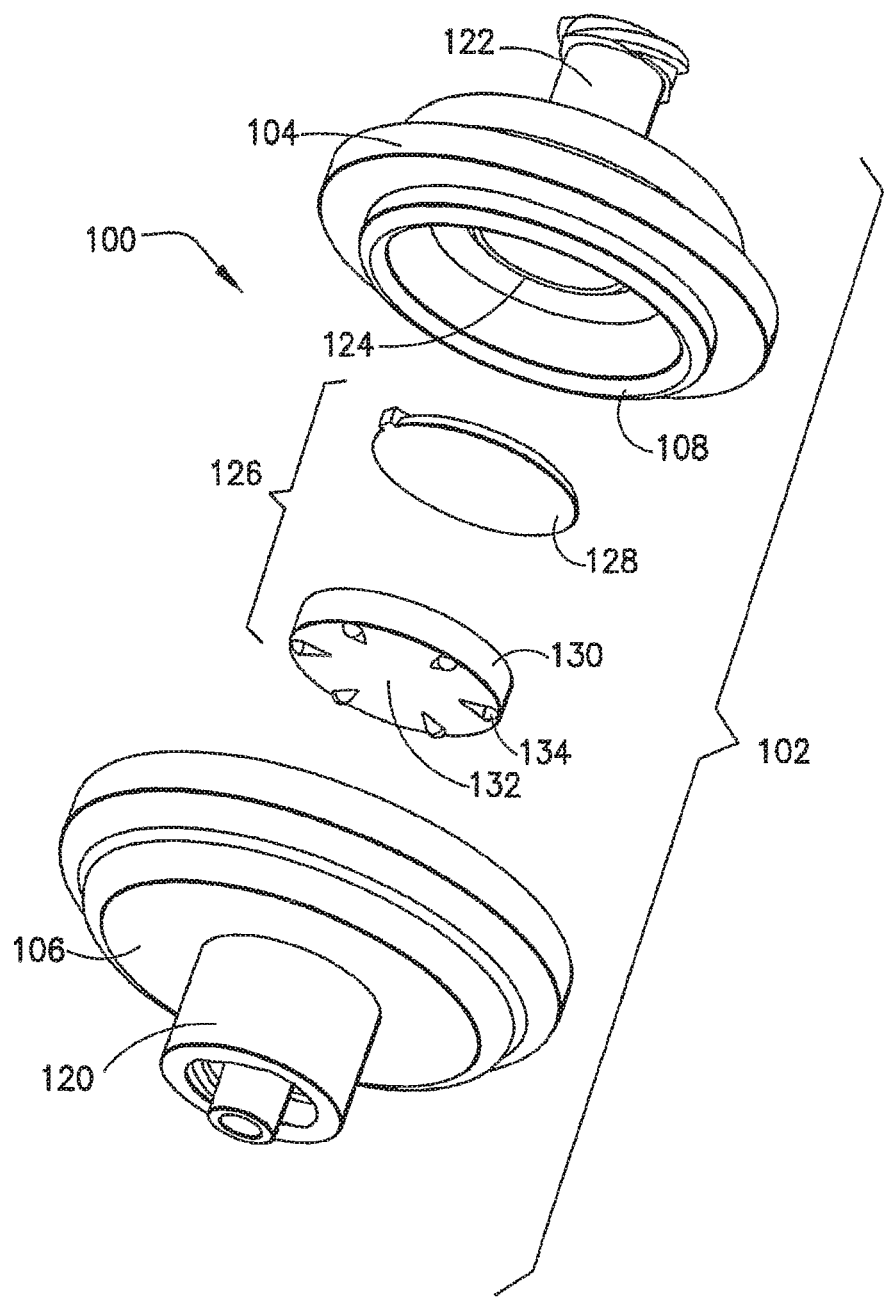
FIG. 4 is an exploded perspective view of the flow-based pressure isolation mechanism of FIG. 3.
Figure 5:
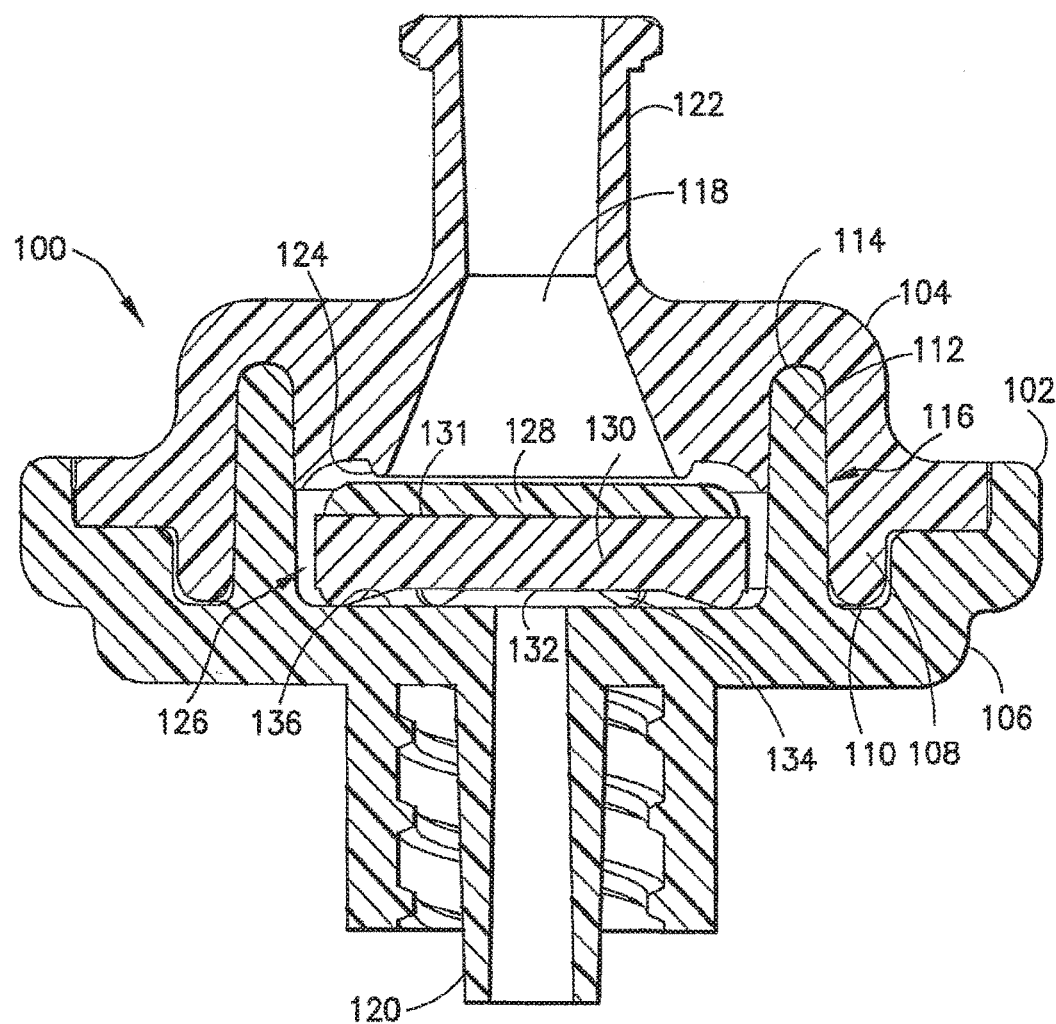
FIG. 5 is a transverse cross-sectional view of the flow-based pressure isolation mechanism of FIG. 3 showing the disk valve member in an open position.

Referring additionally to FIGS. 3-5, pressure isolation mechanism 100 according to one embodiment is shown. Pressure isolation mechanism 100 includes a housing body 102 which may be unitary or desirably provided as a two-piece structure including a first or upper housing portion 104 and a second or lower housing portion 106, which are adapted to connect together to form the housing body 102. As an example, first and second housing portions 104, 106 may be formed for interference engagement with each other and sealed through the use of a medical grade adhesive, or solvent, laser, or ultrasonic weld. Such an interference engagement is formed in part by engagement of a depending outer annular rim 108 formed on first housing portion 104 with a corresponding recess or groove 110, for example, a circumferential or perimetric recess or groove, formed or defined in the second portion 106. Groove 110 may purposely be made slightly smaller in width than the thickness of outer annular rim 108 so that when the first and second housing portions 104, 106 of housing body 102 are joined together there is interference engagement between the outer annular rim 108 and groove 110. Additional interference engagement may be provided between the first and second housing portions 104, 106 of housing body 102 may be accomplished by providing the second housing portion 106 of housing body 102 with a raised inner annular rim 112 that engages or cooperates with a corresponding recess or groove 114, typically a circumferential or perimetric recess or groove, defined in the first housing portion 104. Raised inner annular rim 112 may engage with groove 114 in a similar friction fit—interference engagement manner as outer annular rim 108 cooperates or engages groove 110 in the second housing portion 106 of housing body 102 discussed previously. The combination of the annular rims 108, 112 and grooves 110, 114 generally define a shear interface 116 between the first and second housing portions 104, 106 of housing body 102 which increases their assembly strength. An adhesive, solvent, laser, or ultrasonic weld may be used along shear interface 116 to secure first and second housing portions 104, 106 together. The connection between annular rims 108, 112 and grooves 110, 114 generally defines a tortuous path along this connection line.

First and second housing portions 104, 106 of housing body 102, when secured together, define an internal chamber or cavity 118. Housing body 102 further includes an inlet port 120 in the lower or second housing portion 106 which communicates with internal cavity 118 and an isolation port 122 in the first or upper housing portion 104 also in fluid communication with the internal cavity 118. As illustrated, inlet port 120 and isolation port 122 may be formed as standard luer connectors. In the illustrated embodiment, inlet port 120 is shown as a standard male luer while isolation port 122 is shown as a female luer for exemplary purposes only and this configuration may be reversed. As is apparent from FIG. 2A, inlet port 120 is adapted for connection to pressure transducer port 68 on fitting 58 to associate pressure isolation mechanism 100 with fitting 58 and, thus, fluid path 18. Isolation port 122 is adapted to engage pressure transducer P to fluidly connect the pressure transducer P to fluid path 18. First or upper housing portion 104 defines a seal seat or rim 124 internally within internal cavity 118 that is generally circular in configuration but may take other suitable forms. Generally, seal seat 124 is a raised continuous lip or rim against which a valve element or structure may make a sealing connection or engagement. Seal seat 124 is provided in internal cavity 118 between inlet port 120 and isolation port 122. A valve member 126 is disposed within the internal cavity 118 between inlet port 120 and isolation port 122. Valve member 126 is adapted to engage and seal against seal seat 124 but is disposed within the internal cavity 118 to be free-floating therein. By free-floating it is generally meant that valve member 126 is freely movable within internal cavity 118 in response to fluid flow into inlet port 120 so that the valve member 126 may engage and seal against seal seat 124 to close off fluid flow through internal cavity 118 thereby isolating isolation port 122. Accordingly, valve member 126 is in no way biased in internal cavity 118.

In one form, valve member 126 is generally disk-shaped with the disk-shaped valve member 126 comprised of a disk-shaped member 128 formed of compliant material, such as rubbers or thermoplastic elastomers or silicone, and a stiffening element 130 which is desirably integrally formed with disk member 128 or otherwise secured in permanent or semi-permanent fashion with disk member 128 such as by an adhesive. Stiffening element 130 is desirably formed of a harder plastic material such as polypropylene, polyethylene, or polycarbonate as examples and is suited for supporting disk member 128 which is adapted to seat and seal in engagement with seal seat 124 to seal inlet port 120 from isolation port 122. In operation, valve member 126 is responsive to fluid flow in inlet port 120 so that the valve member 126 may seat and seal against seal seat 124 to form a closed state or condition of pressure isolation mechanism 100. When valve member 126 is not seated against seal seat 124, valve member 126 defines an open state or condition of the pressure isolation mechanism 100. Desirably, the fluid flow in inlet port 120 needed to cause valve member 126 to seat and seal against seal seat 124 and thereby attain a closed state is very small and valve member 126 will seat and seal against seal seat 124 in a near statically closed system due to very small compliance of the pressure transducer P and connecting tubing T associated therewith connected to isolation port 122. This small volume compliance associated with the pressure transducer P and connecting tubing T associated therewith connected to isolation port 122 as well as in the upper portion of internal cavity 118 above valve member 126 is provided or is needed to cause enough forward flow in inlet port 120 to seat the valve member 126 against the seal seat 124 and close the valve member 126.

In addition, this small volume capacitance generates reverse fluid flow in the isolation port 122 that unseats valve member 126 from seal seat 124 when fluid injections are not occurring thereby "opening" the pressure isolation mechanism 100 after a fluid injection procedure. To state the foregoing in another way, the small volume capacitance of pressure transducer P and connecting tubing T generates reverse fluid flow in isolation port 122 and the upper portion of internal cavity 118 above disk member 128 that unseats valve member 126 from seal seat 124 when fluid flow in inlet port 120 is discontinued. Sufficient fluid flow is typically present in inlet port 120 to seat and seal valve member 126 against seal seat 124 when a fluid injection procedure begins using fluid injector 14 and syringe 32 due to this same small volume capacitance and, when fluid injection is complete, flow ceases allowing valve member 126 to unseat from seal seat 124 due to the reverse flow generated by this small volume capacitance upstream of isolation port 122 provided by pressure transducer P and connecting tubing T and that associated with isolation port 122 and the upper portion of internal cavity 118 as well. If the low pressure side of valve member 126, namely, isolation port 122 and pressure transducer P and connecting tubing T, is too ridged then a pressure relief valve 123 could be incorporated into first or upper housing portion 104 to initiate flow and close the valve member 126, or tubing T could be semi-compliant member to allow fluid flow to initiate (in both directions).

Figure 6:
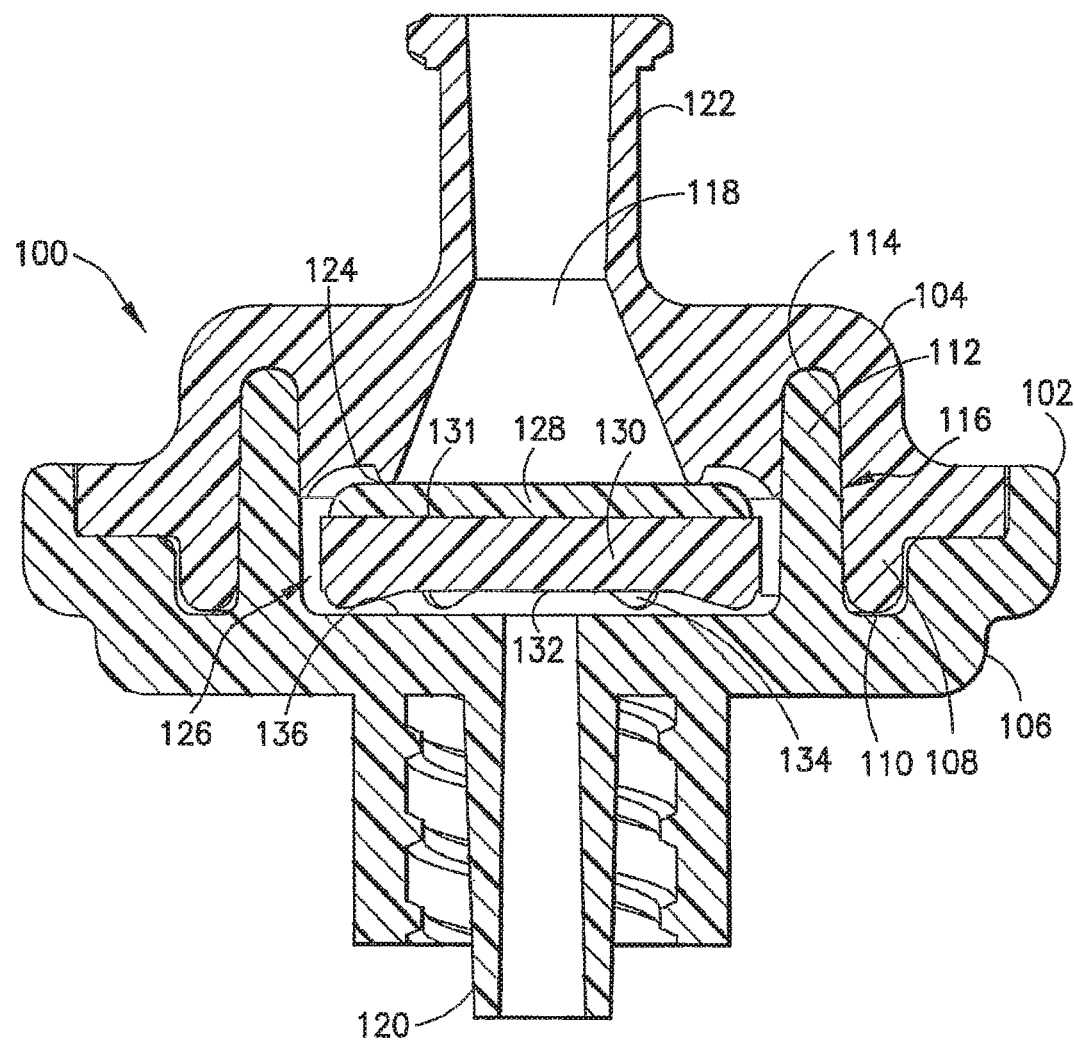
FIG. 6 is a transverse cross-sectional view of the flow-based pressure isolation mechanism of FIG. 3 showing the disk valve member in a closed position.

As shown in FIGS. 5-6, stiffening element 130 is generally positioned in association with disk member 128 to support disk member 128 such that the disk member 128 may form a fluid seal with seal seat 124 to close off fluid flow to isolation port 122 when fluid flow is present in inlet port 120. Moreover, stiffening element 130 includes a top side 131 and a bottom side 132. Structures are provided on the bottom side 132 of stiffening element 130 that face inlet port 120 which prevent the valve member 126 and stiffening element 130, in particular, from forming a seal with the interior of second portion 106 of housing body 102. Such structures located on the bottom side 132 of stiffening element 130 may be in the form of a series of tab members 134 on the bottom side 132 which prevent the stiffening element 130 from collapsing onto an inner surface 136 of the lower or second housing portion 106 of housing body 102, potentially forming a seal with inner surface 136. As FIGS. 5-6 further show, internal cavity 118 and valve member 126 are desirably formed without sharp corners, trapping recesses, or acute angles to minimize the possibility of forming air bubble trap locations in internal cavity 118 which can affect the accuracy of hemodynamic pressure signal readings taken by pressure transducer P as discussed hereinafter. It is noted that the choice of placing tab members 134 on the bottom side of stiffening element 130 (or as part of valve member 126 generally) or forming the same as part of the inner surface 136 of the lower or second housing portion 106 of housing body 102 is a matter only of design choice, and either configuration may be used in any of the embodiments of this disclosure.

Additionally, in the open position or state of valve member 126 fluid communication is present between inlet port 120 and isolation port 122, as shown in FIG. 5, which permits hemodynamic pressure signals to pass via the fluid communication to the pressure transducer P associated with isolation port 122. As described hereinabove, in the closed position of valve member 126, disk member 128 seats against seal seat 124. This may occur, as indicated previously, when fluid flow is present in inlet port 120. However, this may also occur when the pressure isolation mechanism 100 is substantially inverted (i.e., turned upside down) from the orientation shown, for example, in FIG. 5. In this orientation, valve member 126 moves to the closed position under the force of gravity and disk member 128 seats against seal seat 124. Even in this closed position or state of valve member 126, the compliant material that desirably forms disk member 128 allows hemodynamic pressure signals to be transmitted through the body of valve member 126 to pressure transducer P. Thus, it is possible to take accurate hemodynamic pressure signal readings with pressure transducer P in the closed position (as just described) and the open position of pressure isolation mechanism 100 as defined by valve member 126 when a fluid injection procedure is not ongoing. Nonetheless, pressure transducer P remains protected from damaging fluid pressure present at inlet port 120 when a fluid injection procedure commences due to the free-floating, flow-based sealing action of valve member 126.

An advantage of pressure isolation mechanism 100 described hereinabove is that highly accurate hemodynamic pressure signal readings are obtained due to the minimal volume capacitance present in pressure transducer P and connecting tubing T upstream of isolation port 122, as well as in the volume of the isolation port 122 and upper portion of internal cavity 118. Applicants have determined that volume capacitance or termed differently volume compliance in fluid path 18 has an effect on the accuracy of the hemodynamic pressure signal readings taken by pressure transducer P. Volume capacitance or compliance may be described as the change in volume or "swelling" induced in the components of fluid path 18 when under system pressure. In fluid path 18, the components which have the greatest effect on the accuracy of the hemodynamic pressure signal readings taken by pressure transducer P are the connecting tubing T and the volume displacement of pressure transducer P itself. Due to the small or minimized volume capacitance of these components and, further, the small volume capacitance or compliance of isolation port 122 and the upper portion of internal cavity 118 highly accurate hemodynamic pressure signal readings may be taken by the pressure transducer P. Applicants have further determined that numerous variables affect volume compliance or capacitance characteristics of a fluid injection system. These variables include, but are not limited to: tubing size, material resiliency/rigidity, viscosity of fluid in the system, length of fluid travel, and foreign materials present in the fluid including air bubbles. Volume compliance or capacitance may be kept to minimum by limiting tubing size, using more robust materials for system components, limited fluid travel length, and removing foreign matter particularly air bubbles from the fluid path. The short length of connecting tubing T, the rigidity of the material forming housing body 102, and small volume displacement of pressure transducer P limit the volume capacitance or compliance so that accurate hemodynamic pressure signal readings are possible. However, as described previously, some volume capacitance or compliance is provided or is needed first to cause enough forward flow in inlet port 120 to close the valve member 126 when a fluid injection procedure commences and, further, to cause enough reverse fluid flow in isolation port 122 and the upper portion of internal cavity 118 to open valve member 126 after a fluid injection procedure is complete. Therefore, it is undesirable in one context of pressure isolation mechanism 100 to completely eliminate the volume capacitance or compliance associated with isolation port 122 but it is desirable to limit this characteristic to that needed to allow proper functioning of valve member 126, which is to close when a fluid injection procedure commences and open when a fluid injection procedure has been completed or fluid injection ceases for any reason. The foregoing discussion relative to volume capacitance or compliance is applicable to any of the embodiments of pressure isolation mechanism 100 described in this disclosure.

Figure 7:
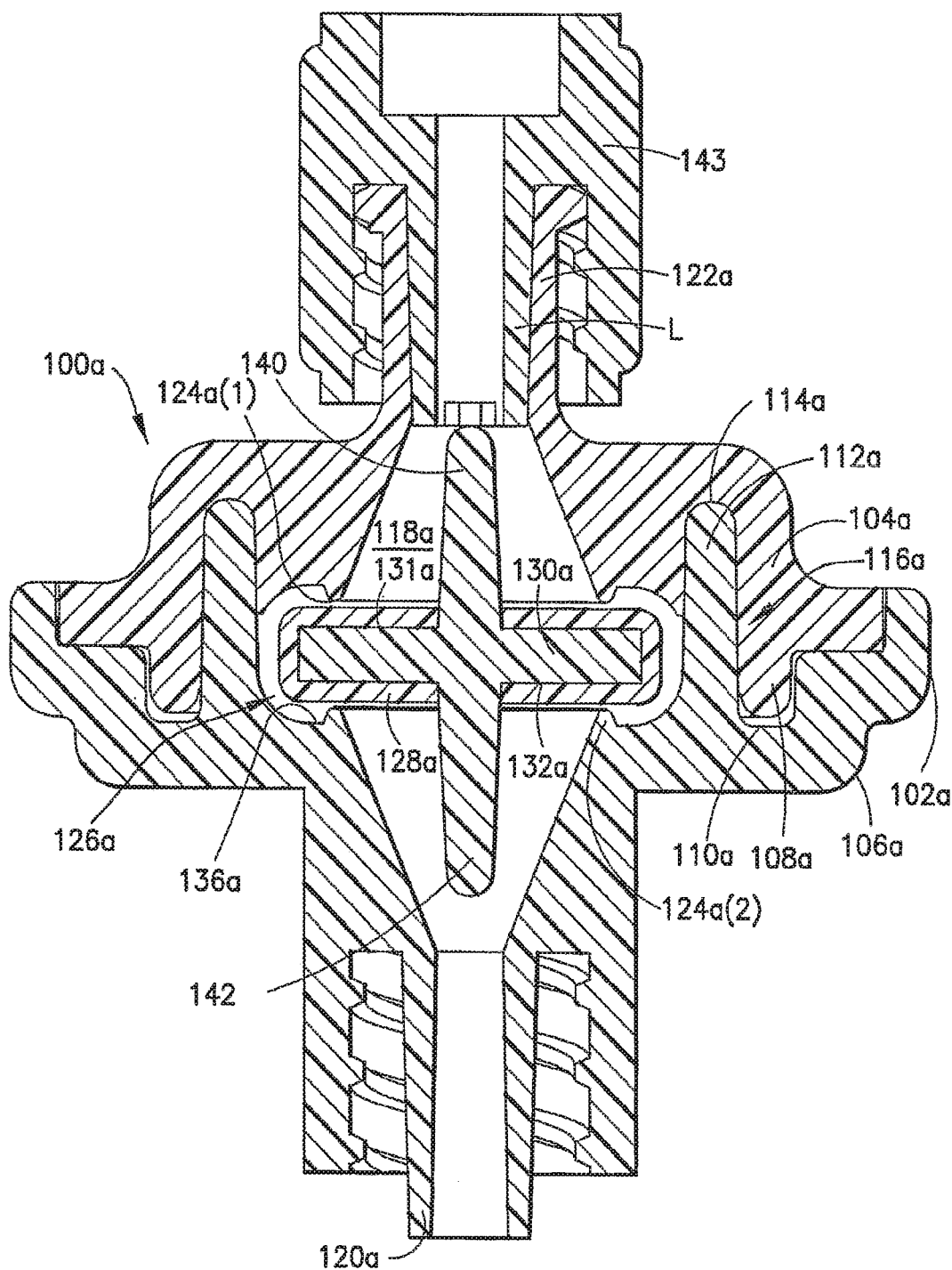
FIG. 7 is a transverse cross-sectional view of the flow-based pressure isolation mechanism of FIG. 3 incorporating an alternative bi-directional flow-responsive valve member.
Figure 8:
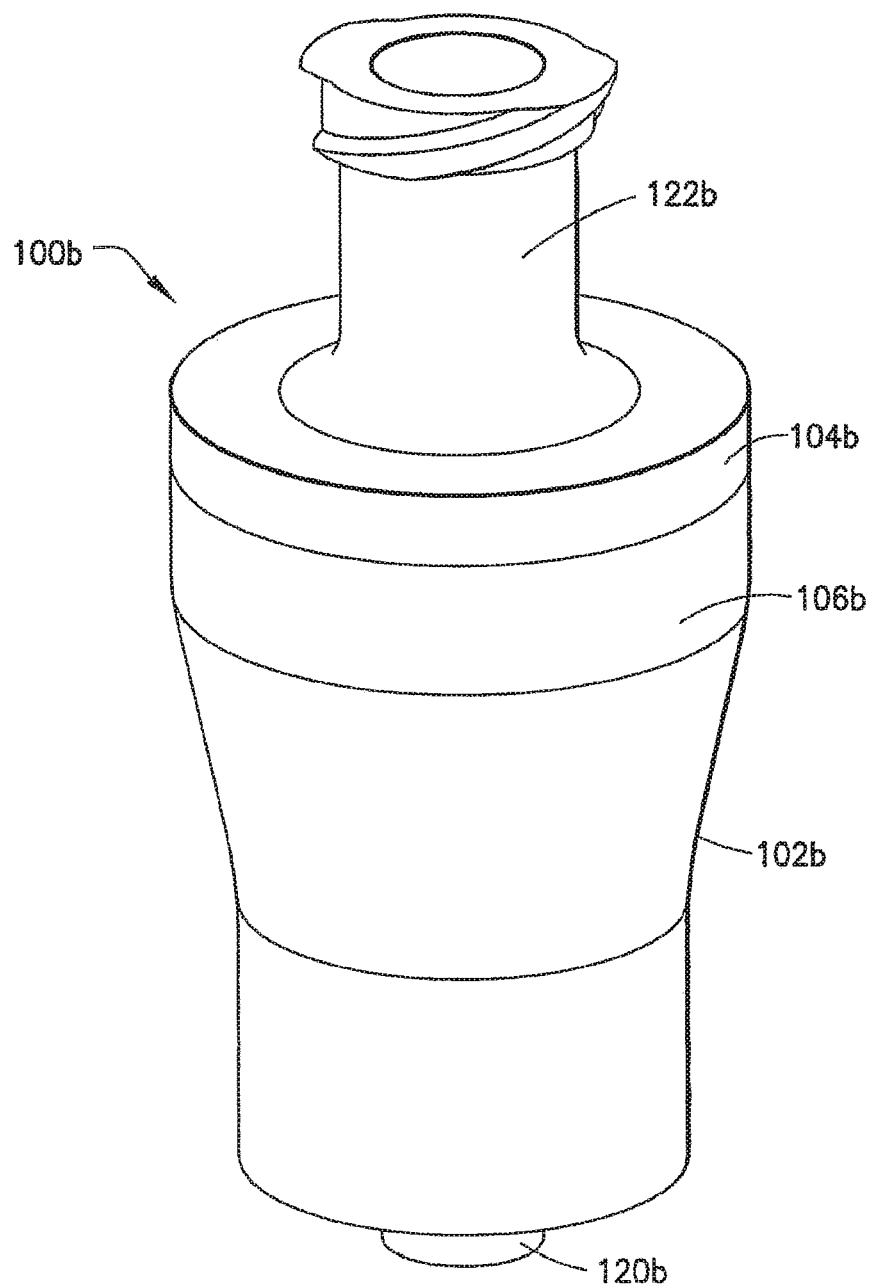
FIG. 8 is a perspective view of a third embodiment of the flow-based pressure isolation mechanism incorporating a flow-responsive valve member in the form of a flow-responsive ball valve member.
Figure 9:
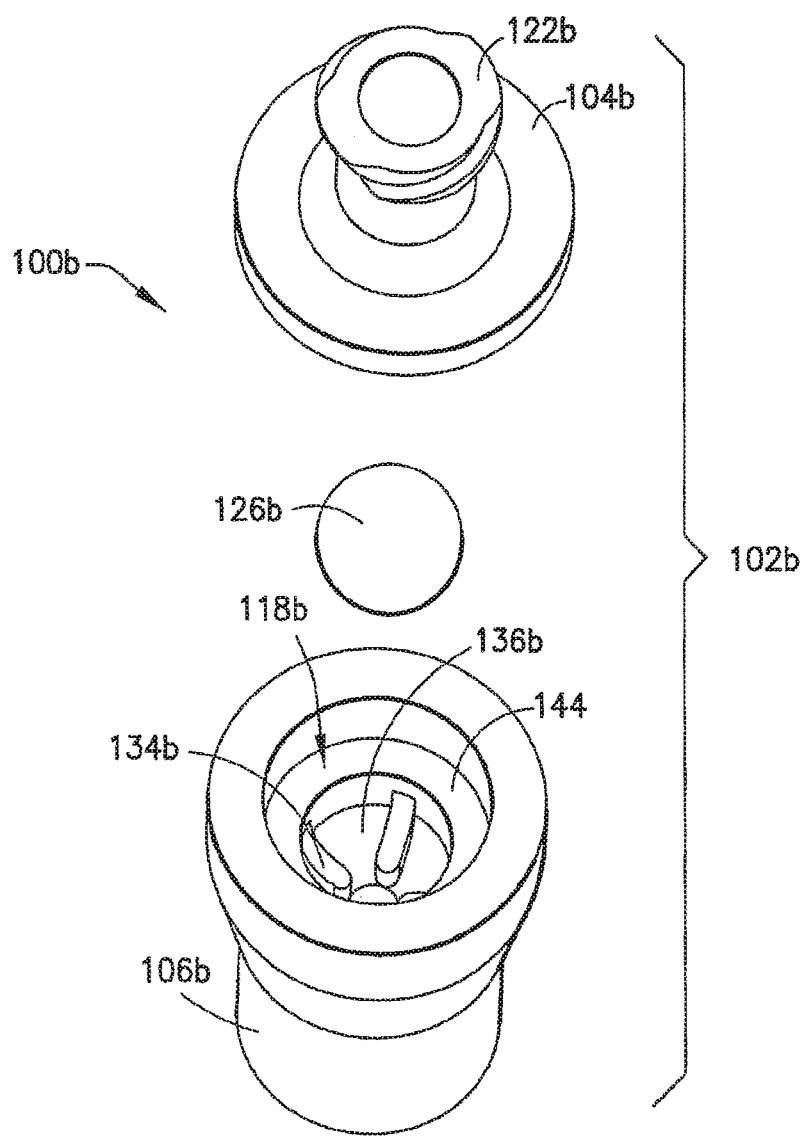
FIG. 9 is an exploded perspective view of the flow-based pressure isolation mechanism of FIG. 8.
Figure 10:
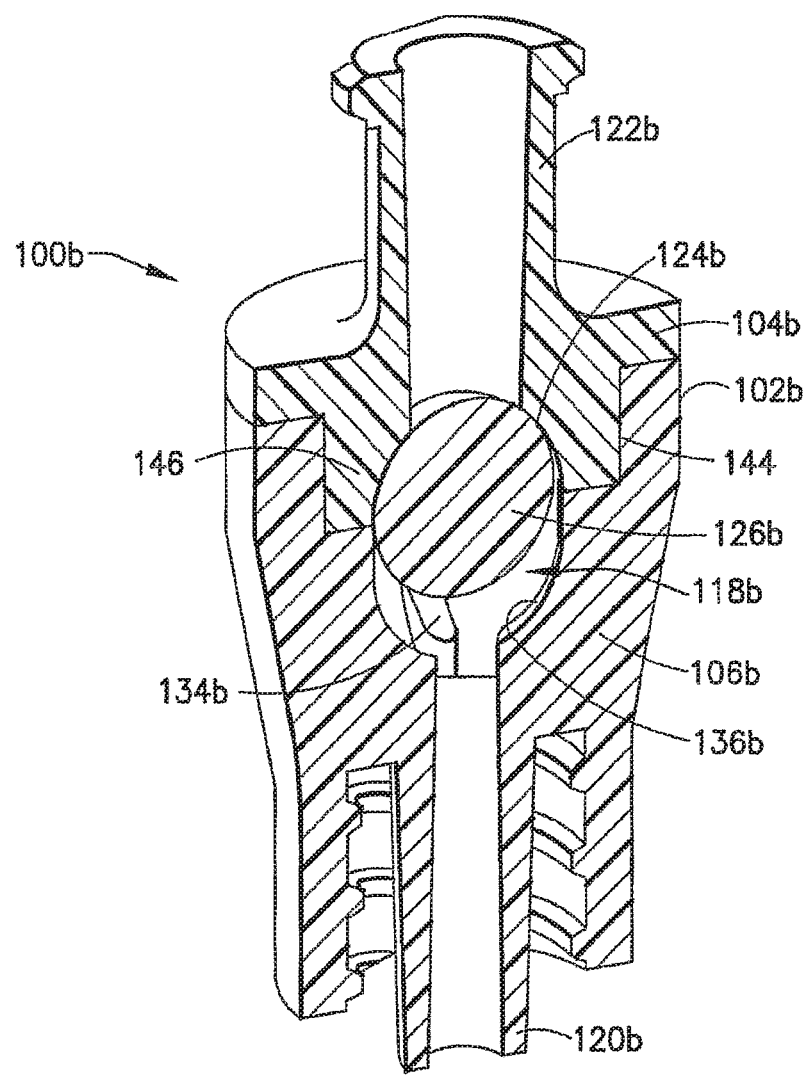
FIG. 10 is a transverse cross-sectional and partially perspective view of the flow-based pressure isolation mechanism of FIG. 8 showing the ball valve member and internal details of the mechanism.

Another embodiment of pressure isolation mechanism 100a is shown in FIG. 7 which is substantially similar in construction to pressure isolation mechanism 100 discussed hereinabove but does not allow free flow of fluid in either direction through internal cavity 118a. In this embodiment, a cap structure 143 is provided as discussed herein to hold the valve member 126a in an open position wherein the valve member 126a does not seat against seal seat 124a to allow purging of air from pressure isolation mechanism 100a prior to using pressure isolation mechanism 100a in fluid path 18. Cap member or structure 143 and its associated use in purging air from the pressure isolation mechanism 100a are described herein. To prevent free flow of fluid in either direction through pressure isolation mechanism 100a, the inner surface 136a of the second or lower housing portion 106a of housing body 102a is formed with an opposing seal seat 124a(2) opposite from seal seat 124a(1) and in place of tab members or structures 134 described previously. Second seal seat 124a(2) is similar in shape and construction to first seal seat 124a(1) and is adapted to coact or engage with the bottom side of valve member 126a to form a fluid seal therewith thereby preventing reverse flow through internal cavity 118a.

In pressure isolation mechanism 100a, it will be noted that stiffening element 130a of valve member 126a is formed with opposing projections 140, 142 extending from top and bottom sides 131a, 132a, respectively, of stiffening element 130a that project within internal cavity 118a toward inlet port 120a and isolation port 122a. Second or lower housing body portion 106a defining inlet port 120a is elongated slightly so that the length of internal cavity 118a is extended along a central axis of housing body 102a. This slight extension of internal cavity 118a accommodates lower projection 142 as illustrated. Additionally, compliant material similar to that used to form disk member 128 described previously encapsulates top and bottom sides 131a, 132a of stiffening element 130a and this compliant encapsulating layer is designated with reference numeral 128a. As FIG. 7 shows, stiffening element 130a is not encapsulated in areas on the top and bottom sides 131a, 132a of stiffening element 130a where projections 140, 142 are provided. From the encapsulated form of stiffening element 130a shown in FIG. 7, it is clear that the encapsulated stiffening element 130a in effect provides opposite facing disk-shaped members 128a on the top and bottom sides 131a, 132a of stiffening element 130 which are analogous to disk member 128 described previously for engaging the respective first and second seal seats 124a(1), 124a(2) to form seals therewith. As a result, valve member 126a is capable of preventing free flow of fluid in either direction through internal cavity 118a.

This embodiment of pressure isolation mechanism 100a operates in the same manner described previously to protect pressure transducer P during a fluid injection procedure. In particular, during a fluid injection procedure valve member 126a is subjected to forward flow in inlet port 120a and closes in the manner described previously to protect pressure transducer P from high pressures during the injection. Additionally, this embodiment of pressure isolation mechanism 100a also protects the pressure transducer P from a potentially damaging vacuum condition which can occur during the course of a reverse flow situation. This protection is provided by the second seal seat 124a(2) and the encapsulated form of valve member 126a providing a "bottom" disk member 128a to seat against seal seat 124a(2) and prevent such a reverse flow situation.

Moreover, the addition of the second seal seat 124a(2) and "bottom" disk member 128a associated with valve member 126a has patient protection applications as well. A reverse flow condition can occur, in one example, if a conventional stopcock is used to connect pressure transducer P to isolation port 122a. If the stopcock is provided with a port that could inadvertently be "opened" to atmospheric pressure, a head pressure differential situation could arise in the fluid path 18 resulting in reverse fluid flow in internal cavity 118a thereby possibly introducing air via Y-T fitting 58 into the disposable first section 40 of the fluid path 18 and, possibly, to the patient. If such a reverse flow situation arises, valve member 126a moves in the reverse direction and closes against the second seal seat 124a(2) and preventing the reverse flow situation from developing.

As indicated previously, projections 140, 142 are unencapsulated by the disk member 128a and this characteristic coupled with their extended length reaching into inlet port 120a and isolation port 122a permits the valve member 126a to be placed into a bi-directional open state. In FIG. 7, cap member 143 is provided and includes a luer tip L. Luer tip L extends sufficiently into isolation port 122a to contact upper projection 140 and, via this engagement or contact, unseat valve member 126a from seal seat 124a. The presence of luer tip L in engagement with projection 140 maintains the orientation of valve member 126a in a bi-directionally open position. As a result, saline or another flushing fluid may be introduced into inlet port 120a and internal cavity 118a to purge air bubbles from internal cavity 118a and isolation port 122a. A three-way stopcock (not shown) may be secured to isolation port 122a after removal of cap member 143 to provide a waste port to complete the purging operation to atmospheric conditions as will be appreciated by those skilled in the art, and, thereafter, pressure transducer P may be connected via connecting tubing T to the stopcock. As an alternative, a pre-purged pressure transducer arrangement may be secured to isolation port 122a (after air purging thereof) without the interposing of a stopcock.

A third embodiment of pressure isolation mechanism 100b is shown in FIGS. 8-12. Pressure isolation mechanism 100b operates in an analogous manner to pressure isolation mechanisms 100, 100a discussed hereinabove but includes several structural differences over these embodiments. Initially, it is noted that housing body 102b is still desirably provided as a two-piece structure including first or upper housing portion 104b and second or lower housing portion 106b, which are adapted to connect together to form the housing body 102b. However, second or lower housing portion 106b is now formed with a central recess 144 which is adapted to receive and accept a depending annular element 146 associated with the first or upper housing portion 104b. The insertion of annular element 146 within central recess 144 may be configured as a friction fit engagement to secure the connection of first and second housing portions 104b, 106b. In this embodiment, a suitable medical grade adhesive is desirably used to secure the engagement of annular element 146 within central recess 144. Other suitable connecting techniques include solvent-based, laser, or ultrasonic welds. As will be noted from FIGS. 8-12, second or lower housing portion 106b has a generally cylindrical appearance while first or upper housing portion 104b forms a cap structure for the cylindrical second housing portion 106b. This change in outward appearance from pressure isolation mechanisms 100, 100a does not affect the operation of pressure isolation mechanism 100b.

First and second housing portions 104b, 106b of housing body 102b, when secured together, define internal chamber or cavity 118b in generally the same manner as discussed previously. Housing body 102b further includes male-luer inlet port 120b in the lower or second housing portion 106b which communicates with internal cavity 118b and female-luer isolation port 122b in the first or upper housing portion 104b also in fluid communication with the internal cavity 118b in the same manner as discussed previously. However, internal cavity 118b of housing body 102b is formed to accept a ball-shaped valve member 126b rather than the generally disk-shaped valve members 126, 126a discussed previously. Ball valve member 126b is again free-floating or freely movable in internal cavity 118b in response to fluid flow in inlet port 120a. By free-floating it is again generally meant that ball valve member 126b in this embodiment is freely movable within internal cavity 118b in response to fluid flow into inlet port 120b so that the valve member 126b may engage and seal against a seal seat 124b which is now formed or defined by an inner surface 148 of first or upper housing portion 104b of housing body 102b. This free-floating movement may include a rotational component in this embodiment.

Figure 11:
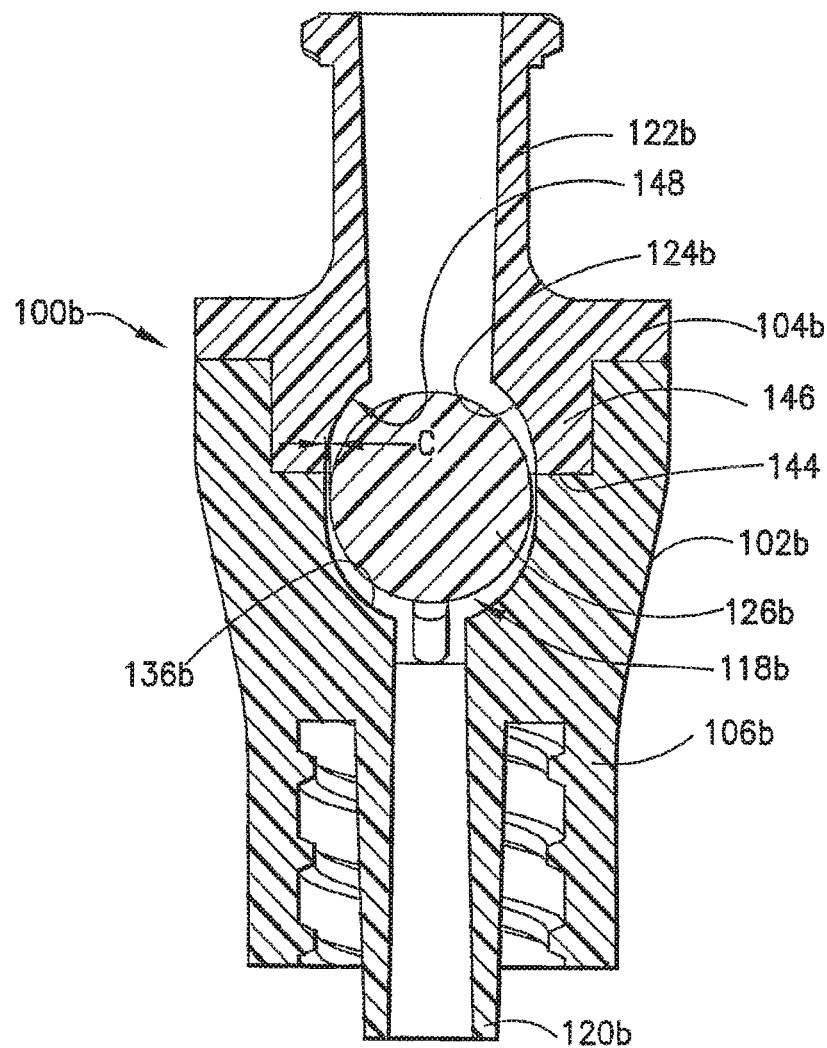
FIG. 11 is a transverse cross-sectional view of the flow-based pressure isolation mechanism of FIG. 8 showing the ball valve member in an open position.
Figure 12:
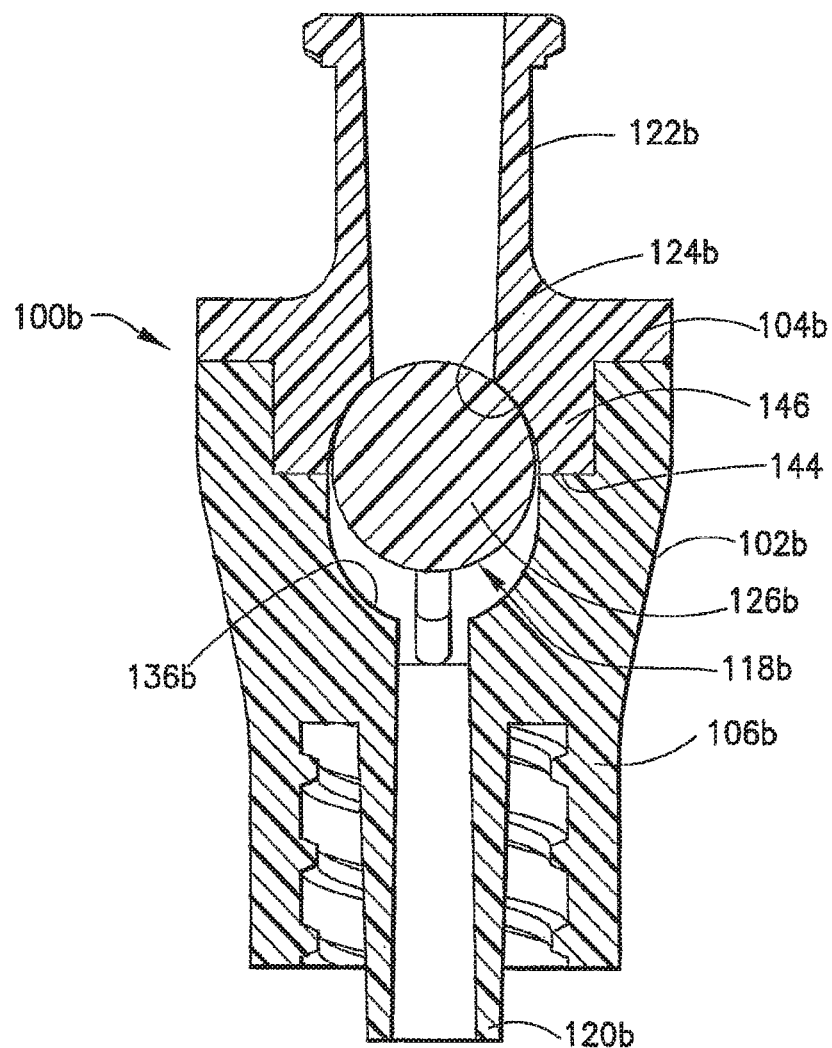
FIG. 12 is a transverse cross-sectional view of the flow-based pressure isolation mechanism of FIG. 8 showing the ball valve member in a closed position.
Figure 13:
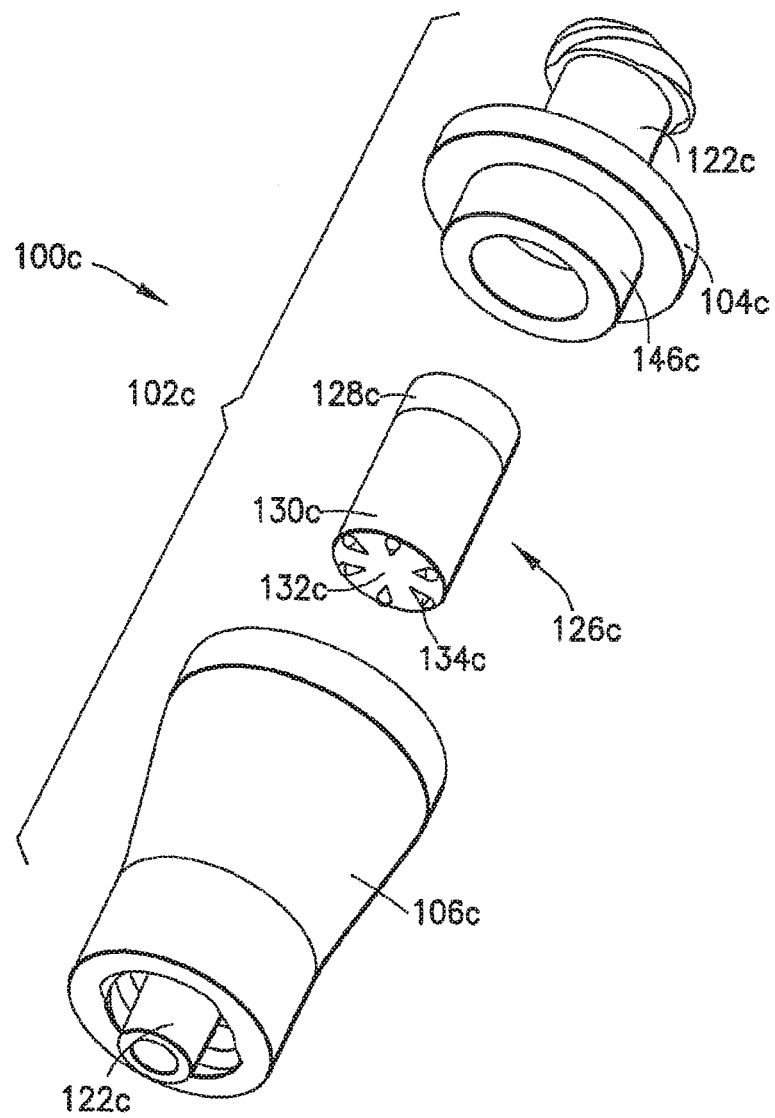
FIG. 13 is an exploded perspective view of a fourth embodiment of the flow-based pressure isolation mechanism incorporating a flow-responsive valve member in the form of a flow-responsive cylinder valve member.
Figure 14:
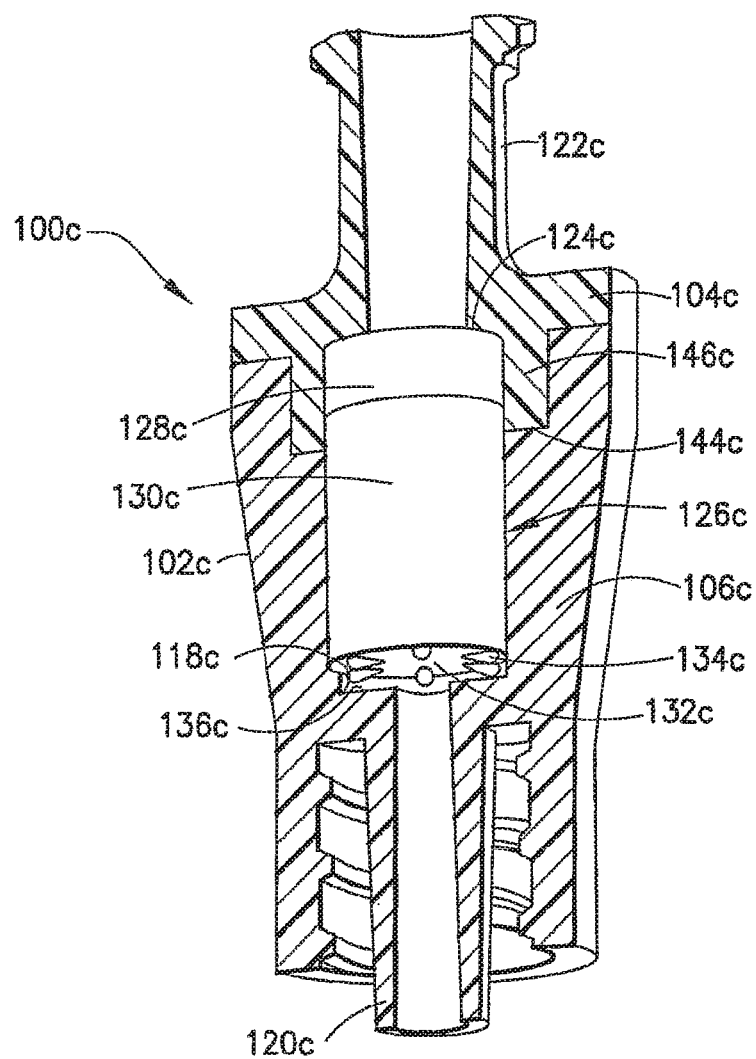
FIG. 14 is a transverse cross-sectional and partially perspective view of the flow-based pressure isolation mechanism of FIG. 13 showing the flow-responsive cylinder valve member and internal details of the mechanism.

As ball valve member 126b seats and seals against inner surface 148 of first housing portion 104b and, in particular, seal seat 124b formed by the inner surface 148, fluid flow through internal cavity 118b is prevented thereby isolating isolation port 122. FIG. 11 illustrates an "open" state of pressure isolation mechanism 100b wherein ball valve member 126b does not engage seal seat 124b. It will be clear that ball valve member 126b is slightly smaller in diameter than the diameter of internal cavity 118b which permits fluid communication between inlet port 120b and isolation port 122b in the open state of pressure isolation mechanism 100b as defined by ball valve member 126b. This fluid communication is represented in FIG. 11 with reference character "C" which represents the clearance between the inner surface 136b of second or lower housing portion 106b of housing body 102b and the perimetric outer surface of ball valve member 126b. In order to prevent ball valve member 126b from closing against the inner surface 136b of the second or lower housing portion 106b of housing body 102b, tab members or structures 134b may also be provided in this embodiment. As with the structure of pressure isolation mechanism 100a discussed previously, tab members or structures 134b are formed on the inner surface 136b of the second or lower housing portion 106b of housing body 102b.

As indicated previously, in the open position or state of ball valve member 126b fluid communication is present between inlet port 120b and isolation port 122b due to the clearance C between the ball valve member 126b and the inner surface 136b of the second or lower housing portion 106b of housing body 102b. This clearance C permits hemodynamic pressure signals to be transmitted to the pressure transducer P through the fluid in internal cavity 118b. Ball valve member 126b is also made of compliant material, such as rubbers or thermoplastic elastomers. Accordingly, in the closed position of ball valve member 126b, for example, when pressure isolation mechanism 100b is inverted as described previously, the compliant material that desirably forms ball valve member 126b allows hemodynamic pressure signals to be transmitted through the body of the ball valve member 126b to the pressure transducer P. Thus, it is possible to take accurate hemodynamic pressure signal readings with pressure transducer P in the closed and open positions or states of pressure isolation mechanism 100b as defined by ball valve member 126b during conditions when a fluid injection procedure is not ongoing. Nonetheless, pressure transducer P remains protected from damaging fluid pressure present at inlet port 120b when a fluid injection procedure commences due to the free-floating, flow-based sealing action of ball valve member 126b.

A fourth embodiment of pressure isolation mechanism 100c is shown in FIGS. 13-16. Pressure isolation mechanism 100c operates in an analogous manner to pressure isolation mechanisms 100, 100a, 100b discussed hereinabove and has the outward appearance of pressure isolation mechanism 100b discussed immediately above. As with pressure isolation mechanism 110b, housing body 102c is desirably provided as a two-piece structure including first or upper housing portion 104c and second or lower housing portion 106c, which are adapted to connect together to form the housing body 102b. As with the immediately foregoing embodiment, second or lower housing portion 106c is now formed with central recess 144c which is adapted to receive and accept depending annular element 146c associated with the first or upper housing portion 104c. The engagement of annular element 146c within central recess 144c may again be configured as a friction fit engagement to secure the connection of first and second housing portions 104c, 106c, with this engagement secured by a suitable medical grade adhesive or other techniques as outlined previously. As with pressure isolation mechanism 100b, second or lower housing portion 106c has a generally cylindrical appearance while first or upper housing portion 104c forms a cap structure for the cylindrical second housing portion 106c. This change in outward appearance does not affect the operation of pressure isolation mechanism 100c.

First and second housing portions 104c, 106c of housing body 102c, when secured together, define internal chamber or cavity 118c in generally the same manner as discussed previously. Housing body 102c further includes male-luer inlet port 120c in the second or lower housing 106c which communicates with internal cavity 118c and female-luer isolation port 122c in the first or upper housing portion 104c also in fluid communication with the internal cavity 118c. As noted previously, the male-female luer configurations may be reversed on inlet port 120c and isolation port 122c. In this embodiment, internal cavity 118c of housing body 102c is now elongated and shaped to accept a cylindrical valve member 126c. Valve member 126c is generally cylindrical-shaped with the cylinder-shaped valve member 126c comprised of disk member 128c formed of compliant material, such as rubbers or thermoplastic elastomers or silicone as outlined previously, and stiffening element 130c which is desirably integrally formed with disk member 128c or otherwise secured in permanent or semi-permanent fashion with disk member 128c such as by an adhesive, as discussed previously. Stiffening element 130c is desirably formed of plastic materials as detailed previously and has a generally cylindrical shape. Stiffening element 130c is generally positioned in association with disk member 128c for supporting disk member 128c to properly engage and seat with seal seat 124c to seal inlet port 120c from isolation port 122c. Moreover, as with valve member 126 discussed previously, stiffening element 130c is provided with tab members 134c on its bottom side 132c facing inlet port 120c which prevents the cylinder valve member 126c from forming a complete seal with the interior or inner surface 136c of second or lower housing portion 106c of housing body 102c.

Cylinder valve member 126c operates in generally the same manner as disk-shaped valve member 126 discussed previously. Accordingly, cylinder valve member 126c is generally responsive to fluid flow in inlet port 120c so that the valve member 126c may seat and seal against seal seat 124c to form a closed state or condition of pressure isolation mechanism 100c. When valve member 126c is not seated against seal seat 124c, valve member 126c defines the open state or condition of the pressure isolation mechanism 100c. Desirably, the fluid flow in inlet port 120c needed to cause valve member 126c to seat and seal against seal seat 124c and thereby close the pressure isolation mechanism 100c is very small and will seat and seal against seal seat 124c in a near statically closed system due to very small compliance of the pressure transducer P and connecting tubing T associated therewith connected to isolation port 122c. This small volume capacitance generates reverse fluid flow in isolation port 122c and the upper portion of internal cavity 118c that unseats valve member 126c from seal seat 124c when fluid injections are not occurring thereby "opening" the pressure isolation mechanism 100c, as described previously. Sufficient fluid flow is typically present in inlet port 120c to seat and seal valve member 126c against seal seat 124c when a fluid injection procedure is ongoing using fluid injector 14 and syringe 32 and, when fluid injection is complete, fluid flow ceases allowing valve member 126c to unseat from seal seat 124c due to the upstream volume capacitance associated with pressure transducer P and connecting tubing T and isolation port 122c.

Figure 15:
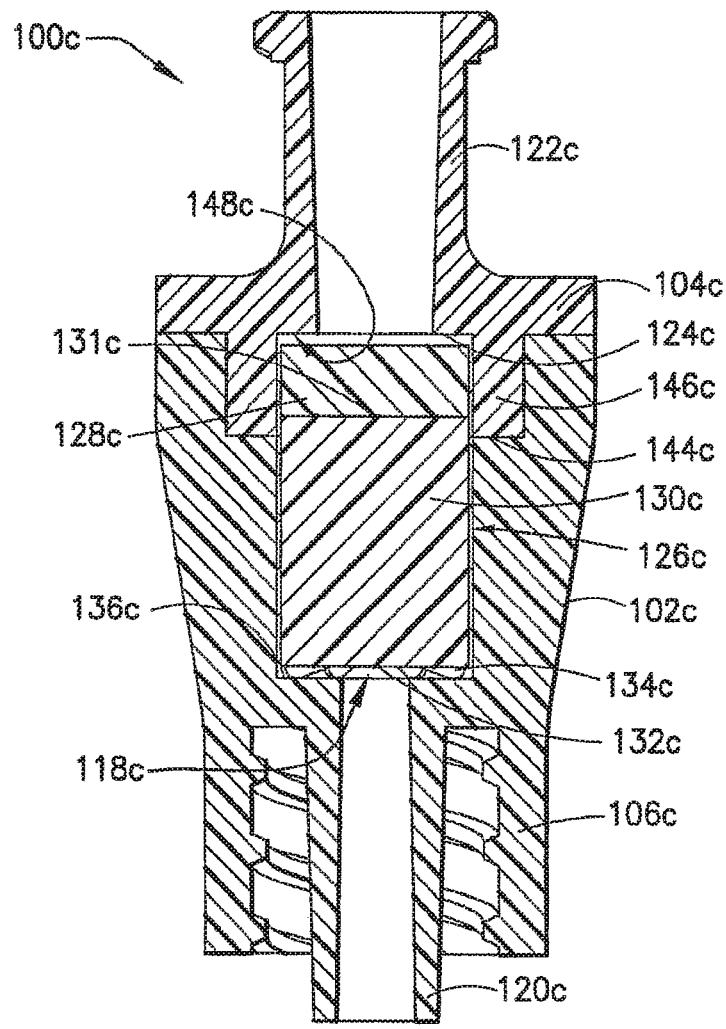
FIG. 15 is a transverse cross-sectional view of the flow-based pressure isolation mechanism of FIG. 13 showing the cylinder valve member in an open position.
Figure 16:
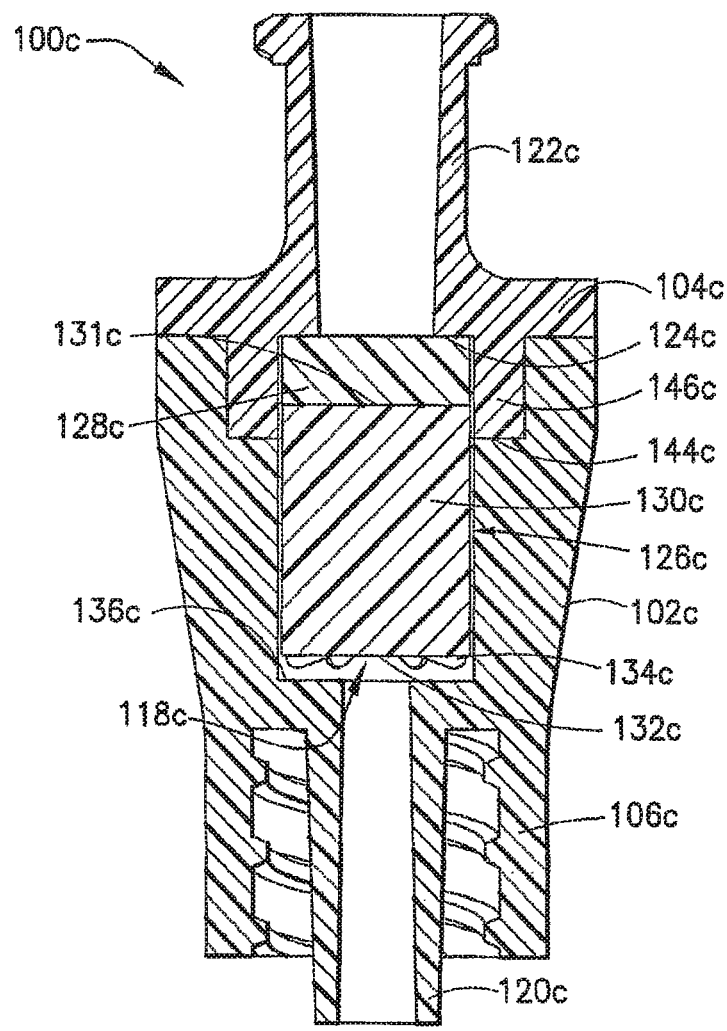
FIG. 16 is a transverse cross-sectional view of the flow-based pressure isolation mechanism of FIG. 13 showing the cylinder valve member in a closed position.
Figure 17:
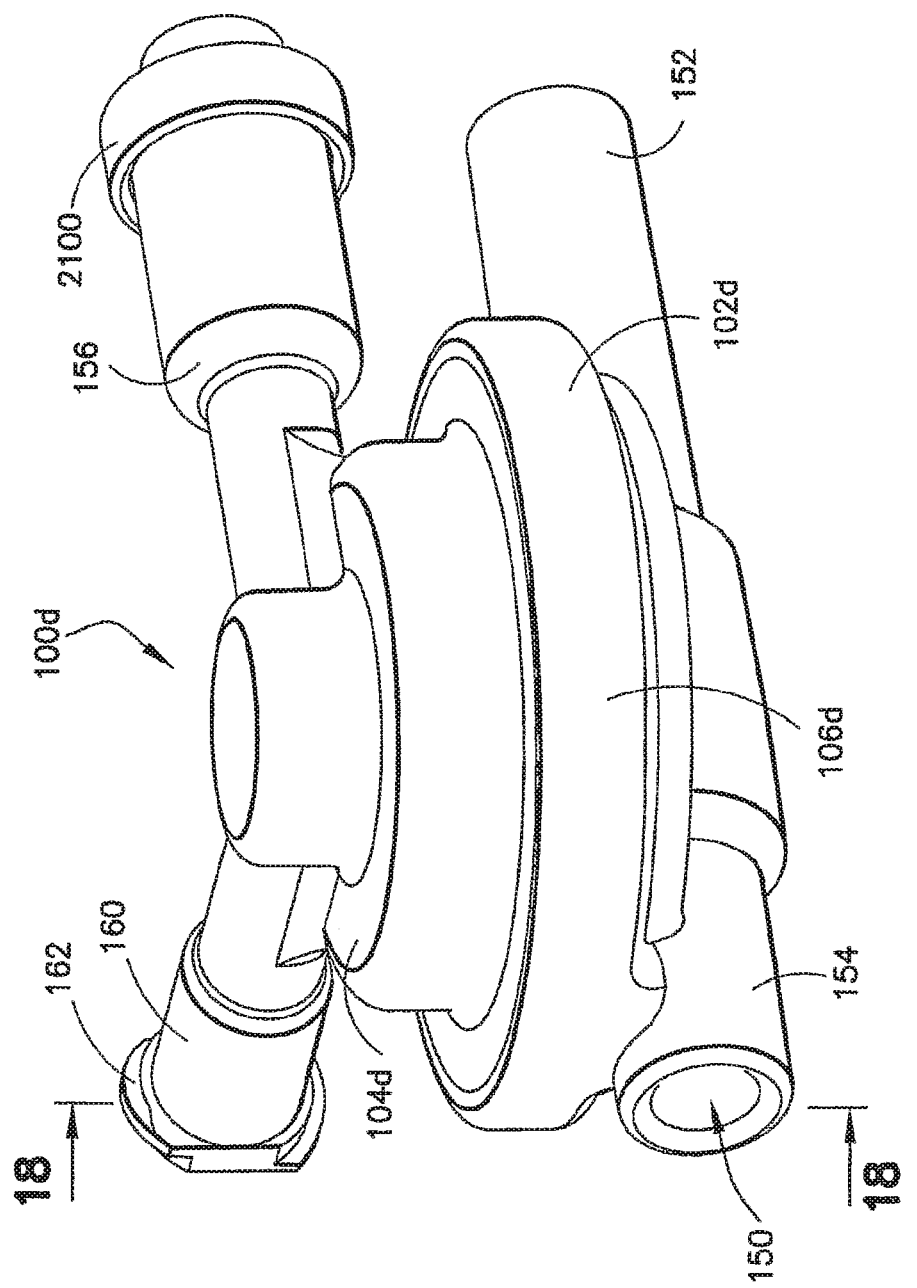
FIG. 17 is a perspective view of a fifth embodiment of the flow-based pressure isolation mechanism having two inlet ports for different fluids and incorporating a flow-responsive valve member in the form of a flow-responsive disk valve member.
Figure 18:
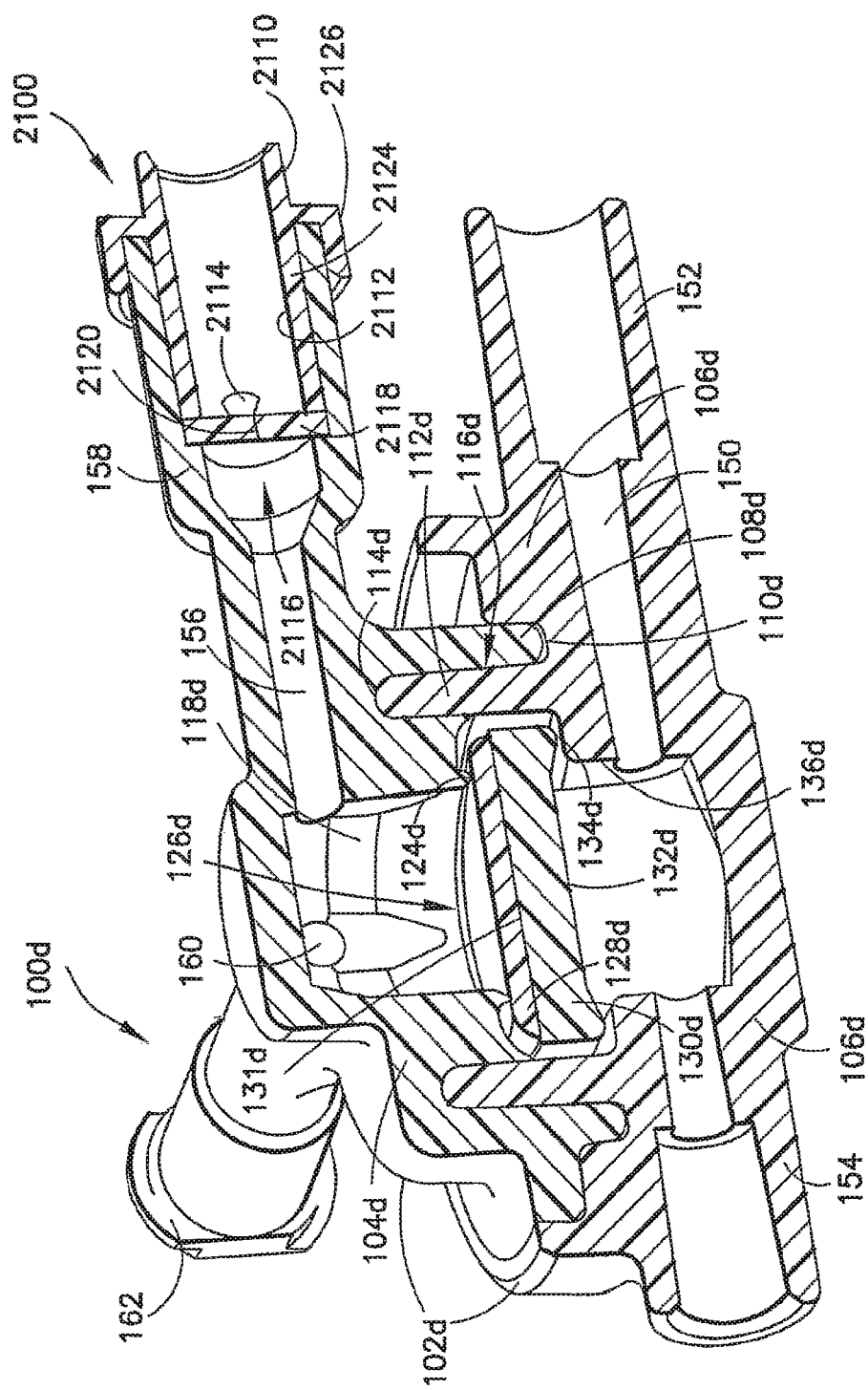
FIG. 18 is a cross-sectional view taken along lines 18-18 in FIG. 17.

Additionally, in the open position or state of valve member 126c fluid communication is present between inlet port 120c and isolation port 122c, as shown in FIG. 15, which permits hemodynamic pressure signals to be transmitted by fluid present in internal cavity 118c to the pressure transducer P associated with isolation port 122c. In the closed position of valve member 126c, for example, when pressure isolation mechanism 100b is inverted as described previously, wherein disk member 128c seats against seal seat 124c, the compliant material that desirably forms disk member 128c allows the hemodynamic pressure signals to be transmitted through the body of valve member 126c to the pressure transducer P. Thus, it is possible to take accurate hemodynamic pressure signal readings with pressure transducer P in the closed and open positions or states of pressure isolation mechanism 100c as defined by valve member 126c during conditions when a fluid injection procedure is not ongoing. Nonetheless, pressure transducer P remains protected from damaging fluid pressure present at inlet port 120c when a fluid injection procedure commences due to the free-floating, flow-based sealing action of cylinder valve member 126c.

Referring to FIGS. 17-23 another embodiment of pressure isolation mechanism 100d is shown. As with previous embodiments, pressure isolation mechanism 100d comprises a housing 102d that may be a unitary housing or, typically, a multi-piece housing including first or upper housing portion 104d and second or lower body portion 106d, which are adapted to connect together in the manner described hereinabove in connection with FIGS. 3-6 in particular. However, pressure isolation mechanism 100d differs from previous embodiments in that housing body 102d is adapted to directly receive or accept fluid connection directly to input lines 64, 66. As indicated previously, first input line 64 is associated with the low pressure fluid delivery system 38 generally and the output line 52 connected to the drip chamber 48 associated with the secondary fluid source 36 in particular. Second input line 66 is associated with the high pressurizing system or device comprised by syringe 32 and fluid injector 14. Second or lower body portion 106d defines a primary or high pressure lumen 150, which forms a high pressure side of pressure isolation mechanism 100d. An inlet port 152 to high pressure or primary lumen 150 is in fluid communication with the second input line 66 which is the high pressure line connecting pressure isolation mechanism 100d with the output line 54 associated with multi-position valve 46 and, ultimately, syringe 32 associated with fluid injector 14. An outlet port 154 of lumen 150 is connected to second multi-position valve 72 by conventional medical connection methods.

First or upper housing portion 104d of housing body 102d defines a secondary or low pressure lumen 156 which generally forms a low pressure side of pressure isolation mechanism 100d. Low pressure lumen 156 has an inlet port 158 that is in fluid communication with first input line 64, which is a low pressure line that connects pressure isolation mechanism 100d to the low pressure fluid delivery system 38. The first or upper housing portion 104d of housing body 102d further includes a pressure isolation port 160 to which a pressure transducer P (illustrated in FIG. 2A) may be connected. Pressure isolation port 160 may terminate in a luer connector for connecting pressure transducer P to luer structure 162 associated with pressure isolation port 160. Pressure isolation port 160 is in fluid communication with low pressure lumen 156 and high pressure lumen 150 via internal cavity 118$d$.

Internal cavity 118$d$ is formed by the first and second housing portions 104$d$, 106$d$ of housing body 102$d$ in generally the same manner as pressure isolation mechanism 100 discussed previously. First or upper housing portion 104$d$ defines seal seat or rim 124$d$ internally within internal cavity 118$d$ in generally the same manner as present in pressure isolation mechanism 100 discussed previously. Accordingly, seal seat 124$d$ is a raised continuous lip or rim against which valve member 126$d$ may make a sealing connection or engagement. Seal seat 124$d$ is provided in internal cavity 118$d$ between high pressure lumen 150 and low pressure lumen 156 and isolation port 160. Valve member 126$d$ is formed in the same manner as valve member 126 discussed previously and is adapted to engage and seal against seal seat 124$d$ in generally the same manner as discussed previously in connection, primarily, with FIGS. 3-6. Accordingly, valve member 126$d$ is disposed within the internal cavity 118$d$ to be free-floating therein. However, valve member 126$d$ is now responsive to fluid flow in high pressure lumen 150 and is freely movable within internal cavity 118$d$ in response to fluid flow high pressure lumen 150 so that the valve member 126$d$ may engage and seal against seal seat 124$d$ to close off fluid flow through internal cavity 118$d$ thereby isolating pressure isolation port 160 and secondary, low pressure lumen 156.

Accordingly, in operation, valve member 126$d$ is generally responsive to fluid flow in high pressure lumen 150 so that the valve member 126$d$ may seat and seal against seal seat 124$d$ to form a closed state or condition of pressure isolation mechanism 100$d$. When valve member 126$d$ is not seated against seal seat 124$d$, valve member 126$d$ defines an open state or condition of the pressure isolation mechanism 100$d$. Desirably, the fluid flow in high pressure lumen 150 needed to cause valve member 126$d$ to seat and seal against seal seat 124$d$ and thereby close the pressure isolation mechanism 100$d$ is very small and will seat and seal against seal seat 124$d$ in a near statically closed system due to very small volumetric capacitance or compliance of the pressure transducer P and connecting tubing T associated therewith connected to pressure isolation port 160 and, further, the volumetric capacitance or compliance of secondary lumen 156. This small volume capacitance or compliance generates reverse fluid flow in pressure isolation port 160$d$ and internal cavity 118$d$ that unseats valve member 126$d$ from seal seat 124$d$ when fluid injections are not occurring thereby "opening" the pressure isolation mechanism 100$d$. As described previously, sufficient fluid flow is typically present in high pressure lumen 150 to seat and seal valve member 126$d$ against seal seat 124$d$ when a fluid injection procedure is ongoing using fluid injector 14 and syringe 32 and when fluid injection is complete, fluid flow ceases allowing valve member 126$d$ to unseat from seal seat 124$d$ due to the small volume capacitance or compliance of the pressure transducer P and connecting tubing T associated therewith connected to pressure isolation port 160 and, further, the volumetric capacitance or compliance of secondary lumen 156. As with valve member 126$d$, stiffening element 130$d$ may have tab members 134$d$ on bottom side 132$d$ to prevent reverse closure of valve member 126$d$ in the manner discussed previously in this disclosure.

Figure 19:
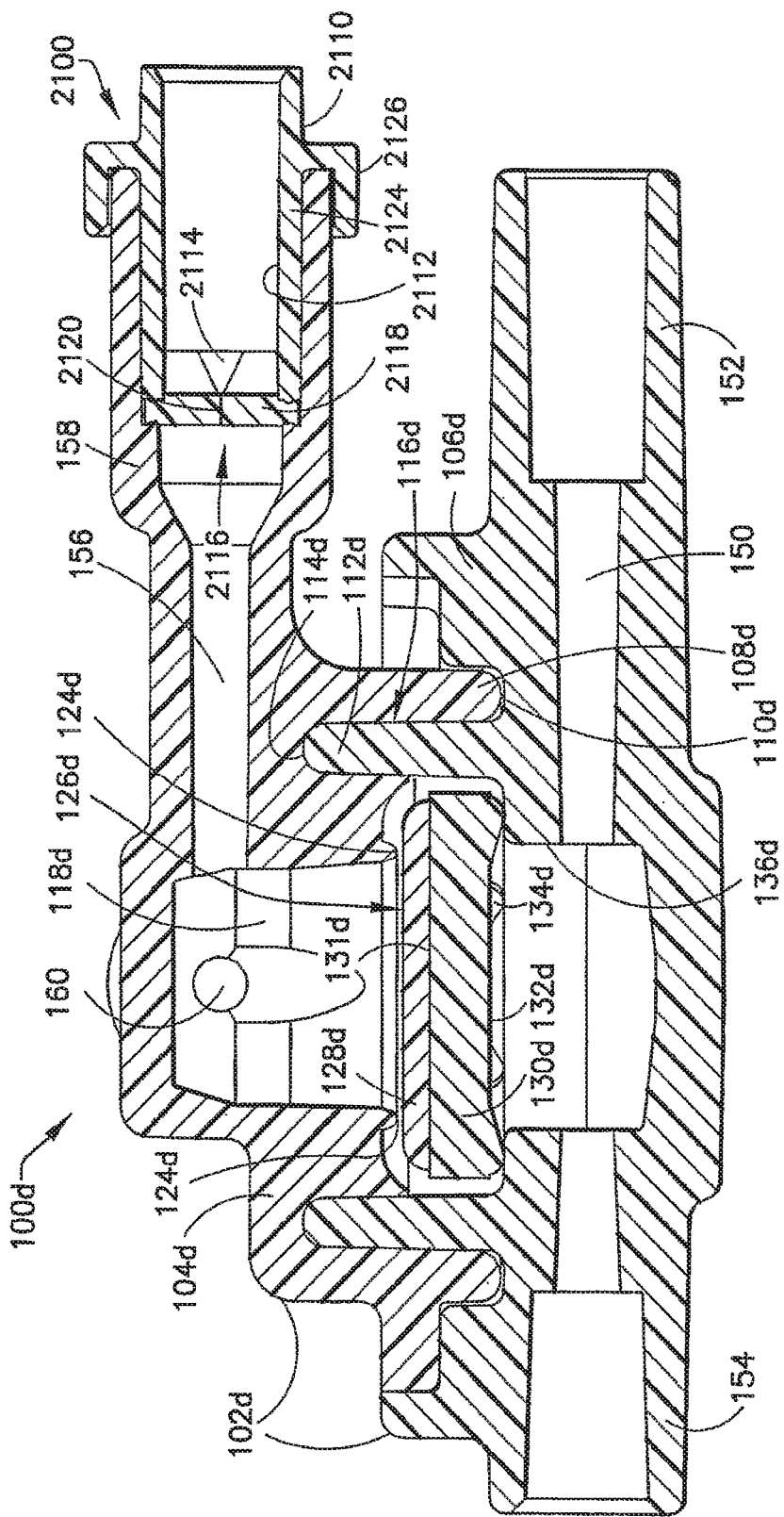
FIG. 19 is a cross-sectional view of the flow-based pressure isolation mechanism of FIG. 17 showing the disk valve member in an open position.
Figure 20:
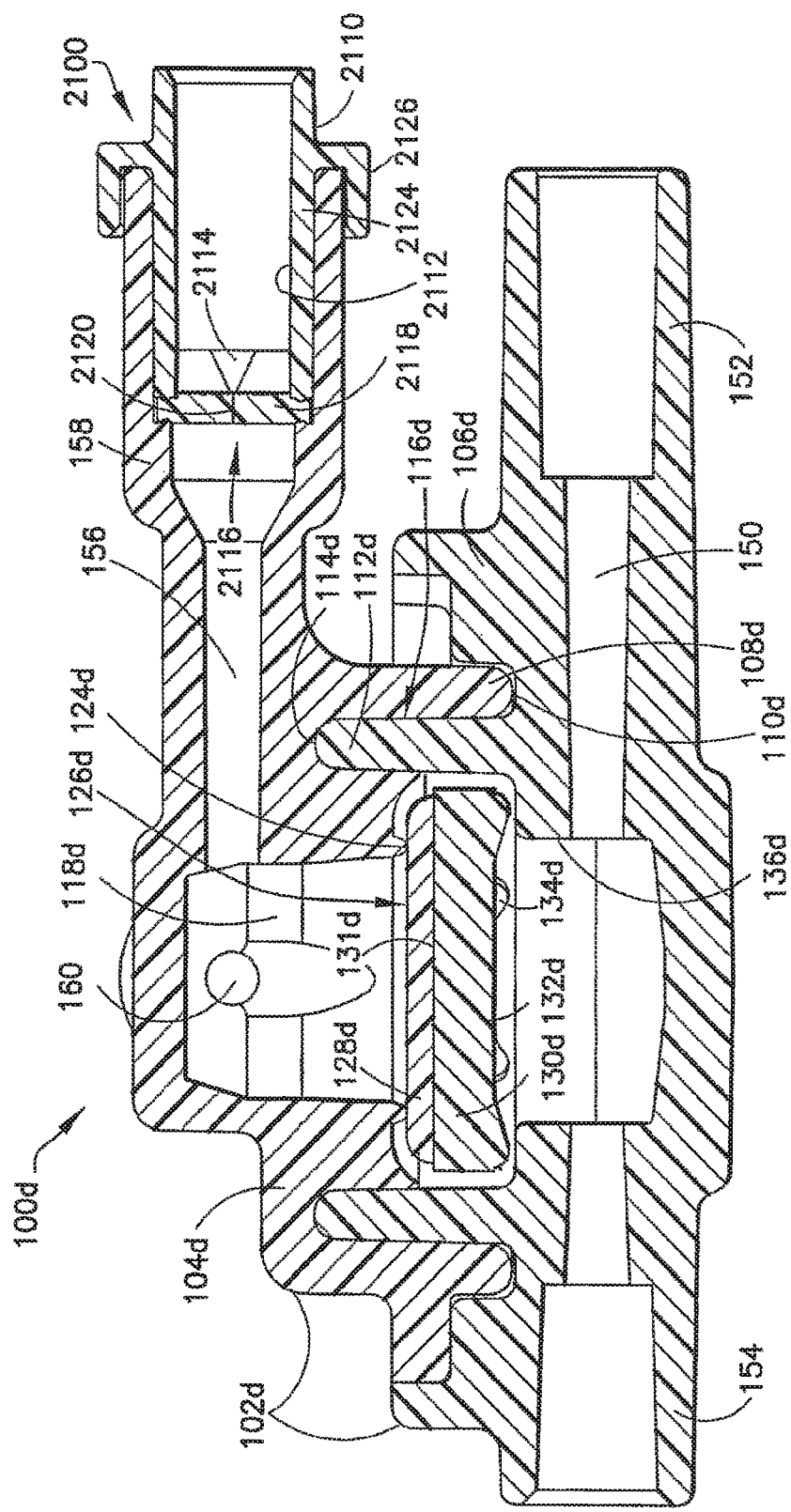
FIG. 20 is a cross-sectional view of the flow-based pressure isolation mechanism of FIG. 16 showing the disk valve member in a closed position.

Additionally, in the open position or state of valve member 126$d$ fluid communication is present between primary lumen 150 and secondary lumen 156 and pressure isolation port 160, as shown in FIG. 19, which permits hemodynamic pressure signals to be transmitted to the pressure transducer P associated with pressure isolation port 160 through fluid present within internal cavity 118$d$. In the closed position of valve member 126$d$, for example, when pressure isolation mechanism 100$d$ is inverted as described previously, wherein disk member 128$d$ seats against seal seat 124$d$, the compliant material that desirably forms disk member 128$d$ allows the hemodynamic pressure signals to be transmitted through the body of valve member 126$d$ to the pressure transducer P. Thus, it is possible to take accurate hemodynamic pressure signal readings with pressure transducer P in the closed and open positions or states of pressure isolation mechanism 100$d$ as defined by valve member 126$d$ during conditions when a fluid injection procedure is not ongoing. Nonetheless, pressure transducer P remains protected from damaging fluid pressure present at inlet port 120$d$ when a fluid injection procedure commences due to the free-floating, flow-based sealing action of valve member 126$d$.

FIGS. 21-24 illustrate a further aspect of pressure isolation mechanism 100$d$. Pressure isolation mechanism 100$d$ as configured to provide accurate undamped hemodynamic pressure readings when saline is present between the patient and the pressure transducer P associated with pressure isolation port 160. However, it is also desirable to provide an undamped signal when contrast is present between the patient and the pressure transducer P. Generally, hemodynamic pressure signals are damped by the presence of air bubbles, thicker fluid media such as contrast, medical tubing lengths, internal diameters, and overall system and tubing compliance, as described previously. The variation of pressure isolation mechanism 100$d$ illustrated in FIGS. 17-24 significantly reduces the dampening of the hemodynamic pressure signals when contrast is present in internal cavity 118$d$ by substantially isolating the compliant tubing associated with the saline, low pressure "side" of the pressure isolation mechanism 100$d$ from the pressure transducer P associated with pressure isolation port 160$d$. This is accomplished in one variation by substantially isolating the compliant tubing and other upstream elements connected with low pressure or secondary lumen 156 with a valve arrangement 2100 disposed in this lumen. Valve arrangement 2100, as will be clear from the following description, allows fluid flow in two directions (bilaterally) in the secondary lumen 156 carrying saline but fluid flow does not start until pressures are above any blood pressure readings.

In general, in pressure isolation mechanism 100$d$, outlet port 154 of primary lumen 150 is associated with a patient, inlet port 152 of primary lumen 150 is associated with syringe 32 and fluid injector 14, and inlet port 158 of secondary lumen 156 is associated with the low pressure saline delivery system 38. Valve arrangement 2100 is generally associated with inlet port 158 of secondary lumen 156 and isolates the "compliant" system components of the low pressure saline fluid delivery system 38 from hemodynamic blood pressure signals from the patient. As a result, these readings are substantially undamped and accurate reading may be taken via a pressure transducer P associated with pressure isolation port 160.

Valve arrangement 2100 comprises an adaptor sleeve 2110 which is sized for mating engagement with the inlet portion or port 158 of secondary lumen 156. Adaptor sleeve 2110 may be an injection molded structure and defines a lumen 2112 therethrough adapted to accept the medical tubing forming first input line 64, which may be adhesively secured in lumen 2112. A stop 2114 is formed in lumen 2112 to limit insertion of first input line 64 in adaptor sleeve 2110. Adaptor sleeve 2110 secures a disk valve 2116 in place within inlet port 158 and across secondary lumen 156. Disk valve 2116 regulates fluid flow bi-laterally through secondary lumen 156 and desirably comprises a stamped disk valve member 2118 made from a flexible thermoplastic material that has one or more slits or openings 2120 through the body of the disk valve member 2118. The number of slits 2120 and length of the slits 2120 control the pressure needed to achieve fluid flow in both directions (bilaterally). Slit disk valves achieve flow control by changing one or more of several design factors as is well-known in the art. For example, slit or passageway opening pressure may be affected by choice of material for the disk valve member 2118, number of slits 2120, length of slits 2120, freedom of deflection/deformation permitted in secondary lumen 156 and/or inlet port 158, and diameter of the secondary lumen 156 and inlet port 158.

Figure 22A:
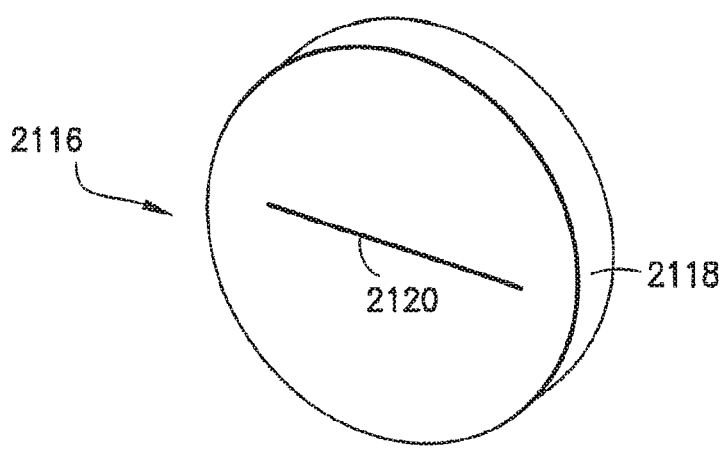
FIGS. 22A-22C are perspective views of respective embodiments of an elastomeric disk valve associated with the valve arrangement of FIG. 21.
Figure 22B:
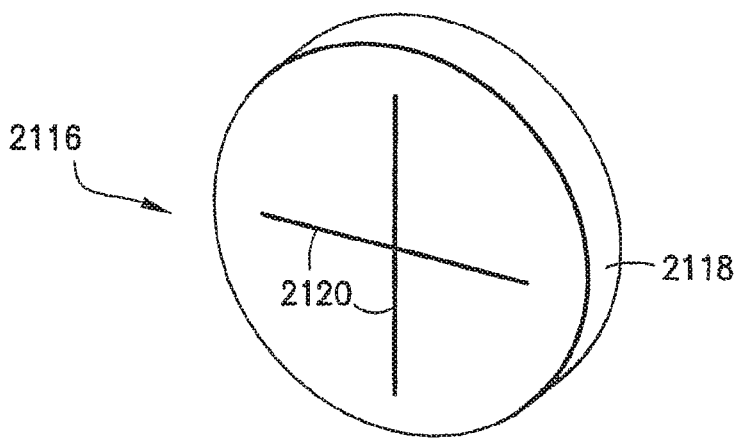
Figure 22C:
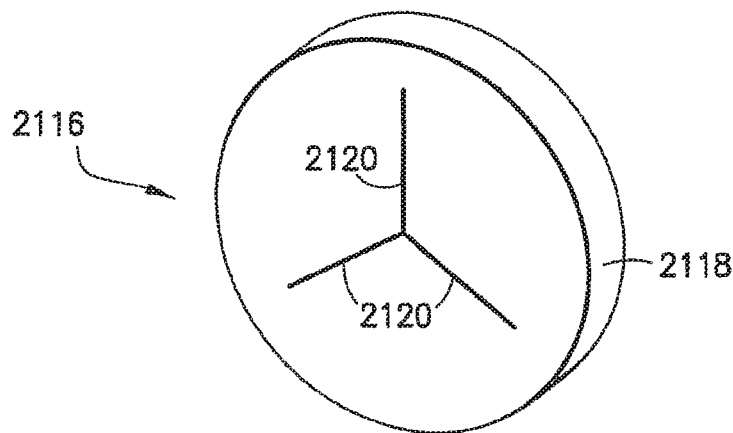

In operation, disk valve 2116 allows fluid flow in both directions and stop 2114 is typically spaced a short distance away from the disk valve member 2118 to provide sufficient spacing or room to allow the disk valve member 2118 to deflect or deform under fluid pressure whereby slits 2120 open and allow fluid flow therethrough. On the opposite side of the disk valve 2116, the secondary lumen 156 may be formed with a shoulder 2122 to restrain the movement or deflection of the disk valve member 2118 in the secondary lumen 156. While the sandwiched arrangement of disk valve member 2118 between shoulder 2122 and stop 2114 may be sufficient to fix the location of the disk valve 2116 in inlet port 158, it is desirable to use a medical grade adhesive around the periphery of disk valve member 2118 to secure the disk valve member 2118 in inlet port 158 and across secondary lumen 156. If desired, a small in-line porous filter valve 2119 may be provided in secondary lumen 156 to add back pressure to limit on pulsatile flow of peristaltic pump 26 and slow down the initial burst of air and fluid when the disk valve 2116 initially operates or opens. FIGS. 22A-22C illustrate disk valve member 2118 with one, two, and three slits 2120, respectively, allow for the changing of opening pressure for valve arrangement 2100. Stop 2114 is generally tapered to allow for the deflecting/deforming movement of disk valve member 2118 in lumen 2112 during operation of disk valve 2116. Disk valve 2116 generally forms a "second" valve structure in pressure isolation mechanism 100*d* in addition to the "first" valve structure in pressure isolation mechanism 100*d* in the form of valve member 126*d*.

Figure 23:
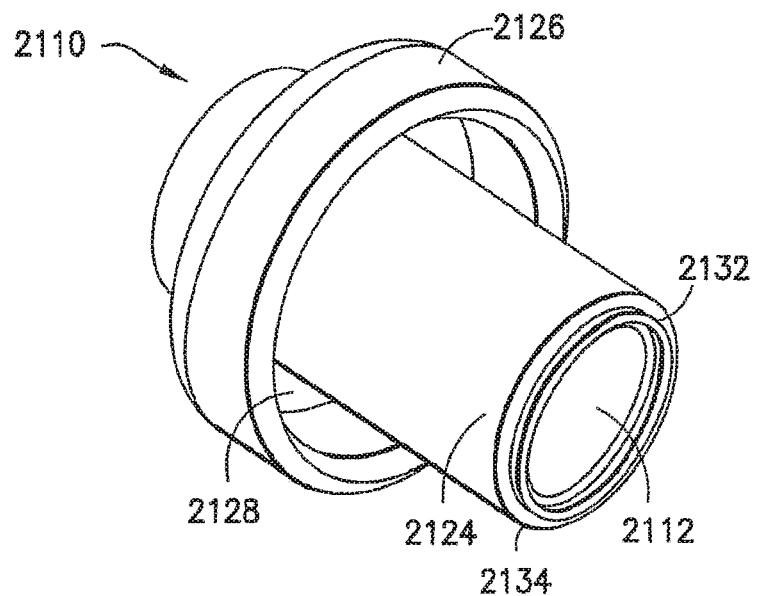
FIG. 23 is a perspective view of a sleeve adaptor used to associate the elastomeric disk valve with the flow-based pressure isolation mechanism.
Figure 24:
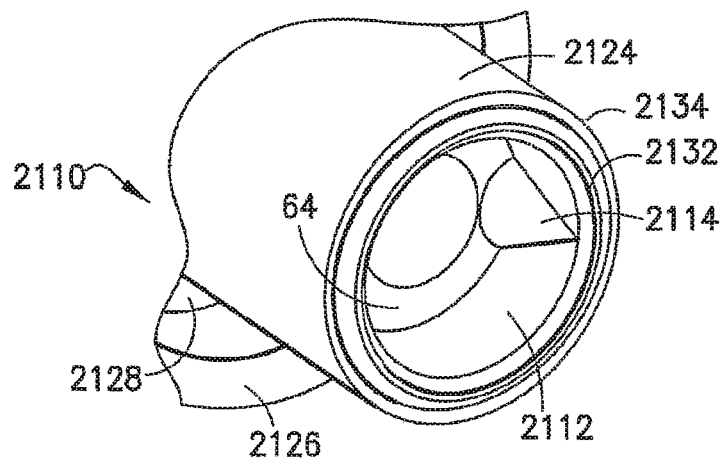
FIG. 24 is a perspective view of a distal end of the sleeve adaptor of FIG. 23.

As shown in FIGS. 23-24, sleeve adaptor 2110 is formed with a tubular body portion 2124 that defines lumen 2112 and an integral annular collar 2126 which extends along the outer side of the tubular body portion 2124. Annular collar 2126 engages or receives the tubular portion of second housing portion 106 of valve housing 1742 which defines the secondary lumen 156 and inlet port 158. Annular collar 2126 defines an annular space 2128 for receiving the inlet port 158 defined by the tubular portion of the second housing portion 106*d* of housing body 102*d*. Inlet port 158 may be secured in annular space 2128 via medical grade adhesive and/or frictional engagement. As revealed by FIGS. 23-24 and FIG. 21, disk valve member 2118 may be formed with a continuous (or alternatively interrupted) recess or groove 2130 adapted to receive a single continuous tab member 2132 (or multiple, discrete tab members 2132) provided on a distal end 2134 of the tubular body portion 2124 of the sleeve adaptor 2110. This inter-engagement between the tab member 2132 and the recess or groove 2130 in the disk valve member 2118 helps to secure the engagement between disk valve 2116 and sleeve adaptor 2110 in inlet port 158. The inter-engagement between the tab member 2132 and the recess or groove 2130 in disk valve member 2118 may be supplemented with a medical grade adhesive if desired.

Figure 25:
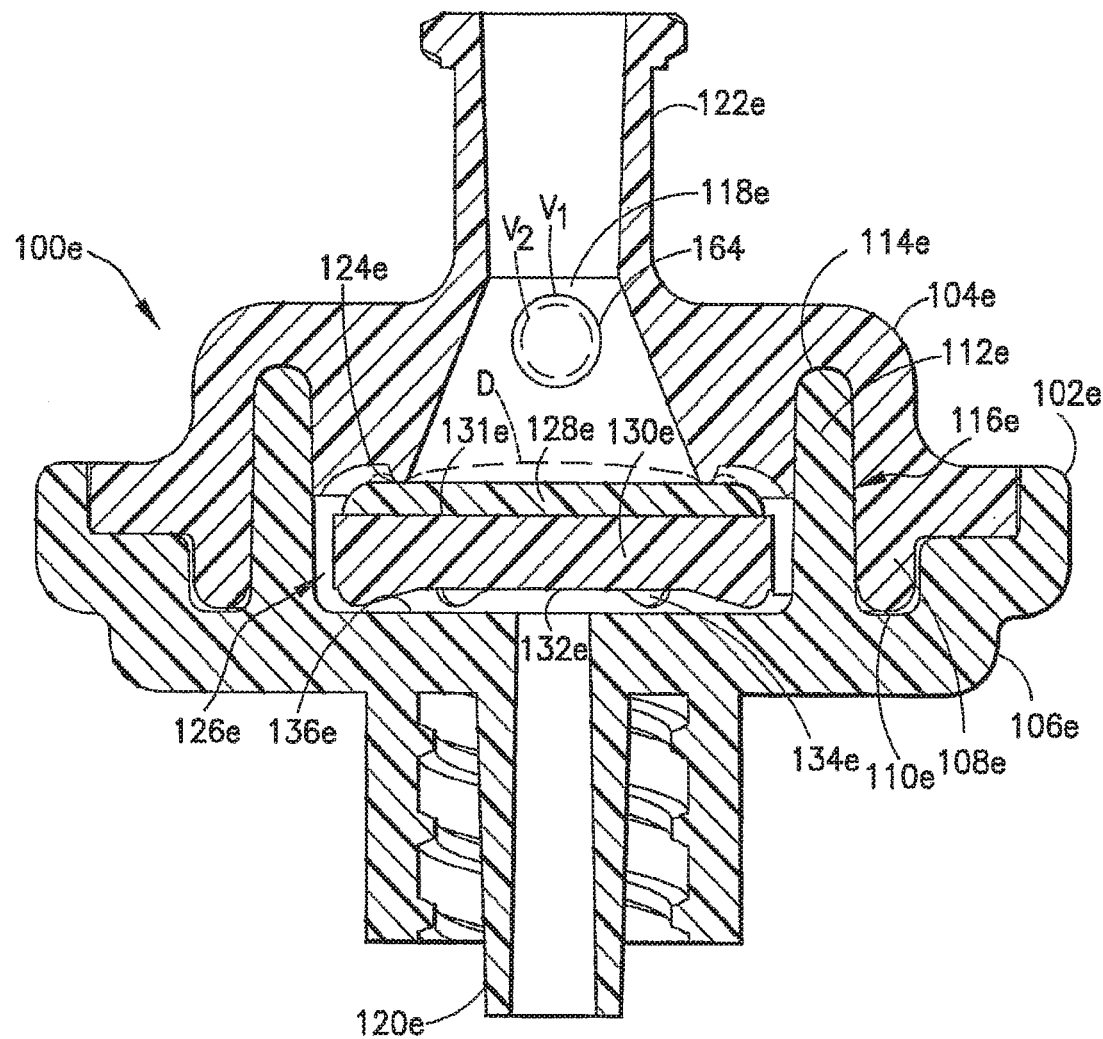
FIG. 25 is a cross-sectional view of a sixth embodiment of the flow-based pressure isolation mechanism incorporating a flow-responsive valve member in the form of a flow-responsive disk valve member and a volumetric capacitance element in the isolation port.
Figure 26:
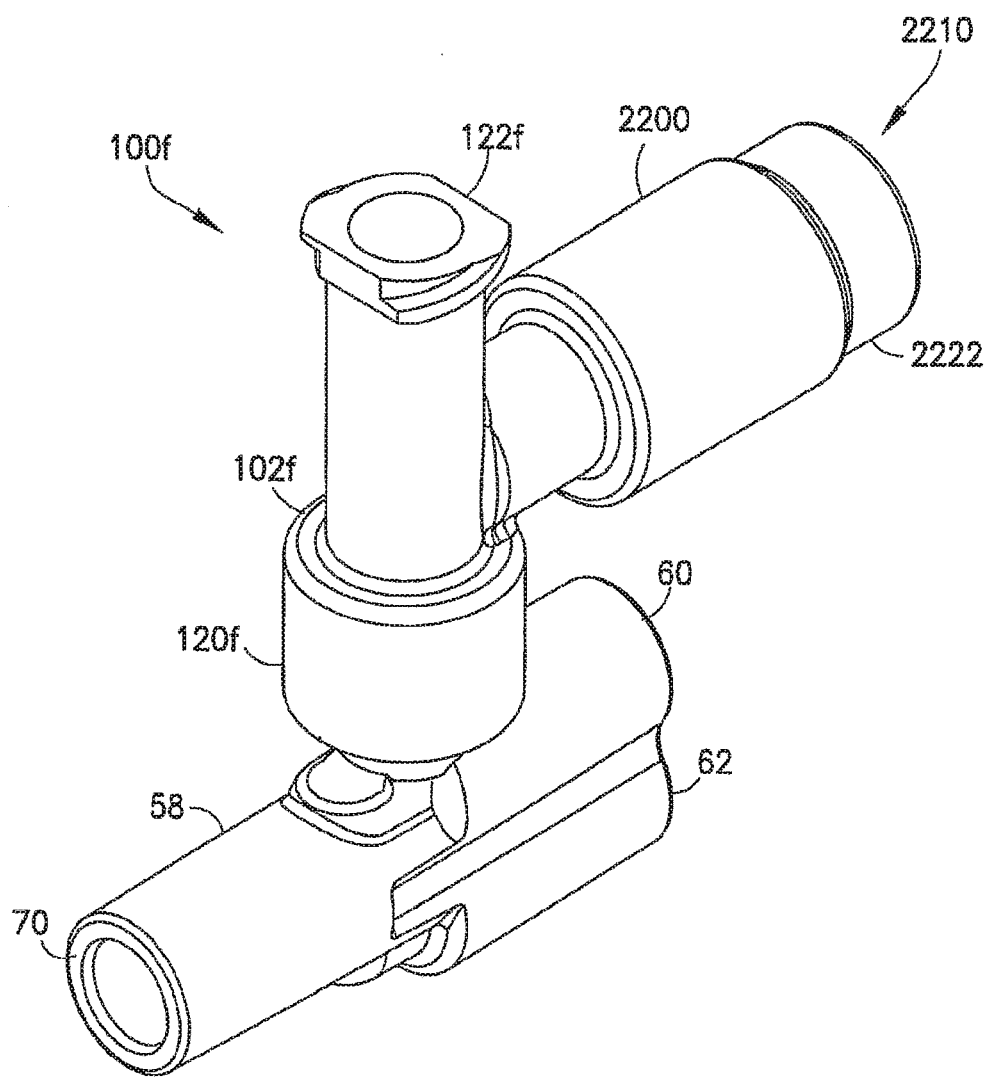
FIG. 26 is a perspective view of another embodiment of the flow-based pressure isolation mechanism incorporating a flow-responsive valve member in the form of a flow-responsive disk valve member.

A further embodiment of pressure isolation mechanism 100*e* is shown in FIG. 25. Pressure isolation mechanism 100*e* operates in an analogous manner to pressure isolation mechanism 100 discussed hereinabove and has the same outward appearance of pressure isolation mechanism 100 discussed immediately above. As a result, the following discussion relating to pressure isolation mechanism 100*e* will concentrate only the differences between pressure isolation mechanism 100*e* and pressure isolation mechanism 100. In pressure isolation mechanism 100*e*, a volumetric capacitance or compliance element 164 is disposed or added in internal cavity 118*e*. While volumetric capacitance element 164 is shown disposed in internal cavity 118*e*, this element may be formed as part of disk member 128*e* of valve member 126*e* or be disposed in isolation port 122*e* or possibly be formed as part of upper housing portion 104*e* and disposed or oriented in internal cavity 118*e* or isolation port 122*e*. Volumetric capacitance element 164 is also desirably made of compliant material and is provided to increase the volumetric capacitance or compliance of the low pressure side of pressure isolation mechanism 100*e* upstream of (above) valve member 126*e* thereby providing extra capacitance to initiate forward or reverse fluid flow in isolation port 122*e* and internal cavity 118*e* to cause valve member 126*e* to seat or unseat from seal seat 124*e*. While volumetric capacitance element 164 may be made of compliant material, it is desirably made of a cellular or porous material to be configured as a hollow member to allow compression thereof and reduction in volume under fluid pressure in internal cavity 118*e*.

In FIG. 25, reference character D represents an exaggerated deformation of disk member 128*e* of valve member 126*e* resulting from fluid pressure in inlet port 120*e* acting on valve member 126*e* when a fluid injection procedure is ongoing and after the disk member 128*e* has been moved into engagement with seal seat 124*e*. This deformation D occurs due to the compliant nature of the material of disk member 128*e* and causes disk member D to deform into the upper portion of internal cavity 118*e*. As a result, the upper portion of internal cavity 118*e* is reduced in volume by the volume occupied by deformation D thereby increasing fluid pressure in the internal cavity 118*e*. This increased fluid pressure likewise acts on volumetric capacitance element 164 reducing its volume from an initial volume $V_1$ to an exaggerated reduced volume identified with reference character $V_2$. This change in volume "stores" volume capacitance or compliance that may be used to assist the given system compliance or capacitance in opening valve member 126*e* after the fluid injection procedure is completed. When the fluid injection procedure is discontinued, fluid pressure acting on the bottom side 132*e* of stiffening element 130*e* is reduced and the disk member 128*e* resiliently returns to its normal state and the volumetric capacitance element 164 expands to its normal volume thereby assisting in generating the reverse fluid flow in isolation port 122*e* and the upper portion of internal cavity 118*e* needed to unseat valve member 126*e* from seal seat 124*e* to place the valve member 126*e* in the open state.

An additional embodiment of pressure isolation mechanism 100*f* is shown in FIGS. 26-29. Pressure isolation mechanism 100*f* is provided as part of disposable second section 42 of fluid path 18 (FIGS. 2A and 2B) in the manner described previously in this disclosure and is associated with Y-T fitting 58 in a generally similar manner as described previously in this disclosure. As with previously-described embodiments, pressure isolation mechanism 100*f* serves several functions in fluid delivery system 12 but is primarily provided to connect pressure transducer P to fluid path 18 so that hemodynamic blood pressure signal readings may be obtained during fluid delivery procedures involving fluid delivery system 12. Further details of pressure isolation mechanism 100*f* are provided hereinafter.

As described previously, Y-T fitting 58 includes two input ports 60, 62 respectively connected to input lines 64, 66 as shown in FIG. 2A discussed previously. Y-T fitting 58 serves as the physical merge point for primary and secondary injection fluid paths for delivery of contrast and saline as examples to a patient via a catheter during a fluid injection or delivery procedure. Input lines 64, 66 as discussed hereinabove comprise a first input line 64 associated with the low pressure fluid delivery system 38 generally and output line 52 connected to drip chamber 48 associated with secondary fluid source 36 in particular, and a second input line 66 associated with high pressure system or device comprised by syringe 32 and fluid injector 14 (see FIG. 2B). As further described previously, Y-T fitting 58 has a pressure transducer port 68 and an outlet port 70.

Figure 27:
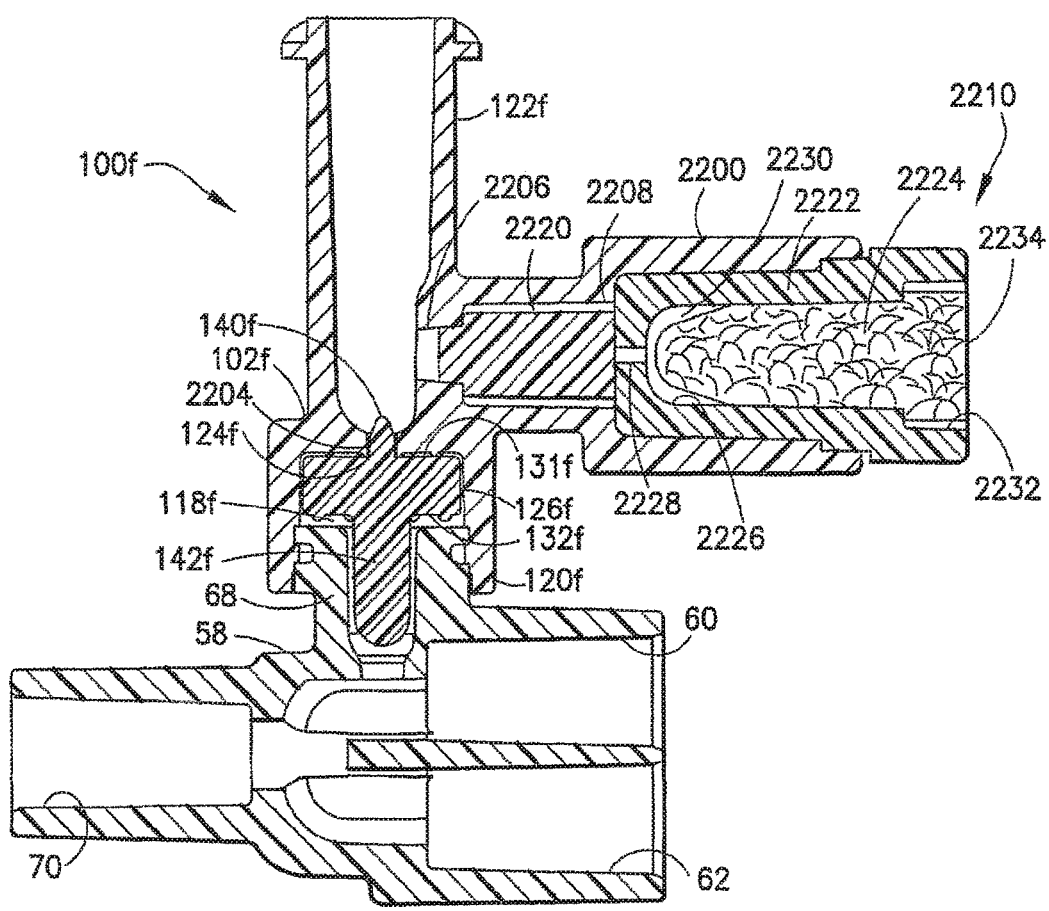
FIG. 27 is a transverse cross-sectional view of the flow-based pressure isolation mechanism of FIG. 26 showing the disk valve member in a closed position and the flow-based pressure isolation mechanism associated with an element of the fluid path set of FIGS. 1 and 2A-2B.
Figure 28:
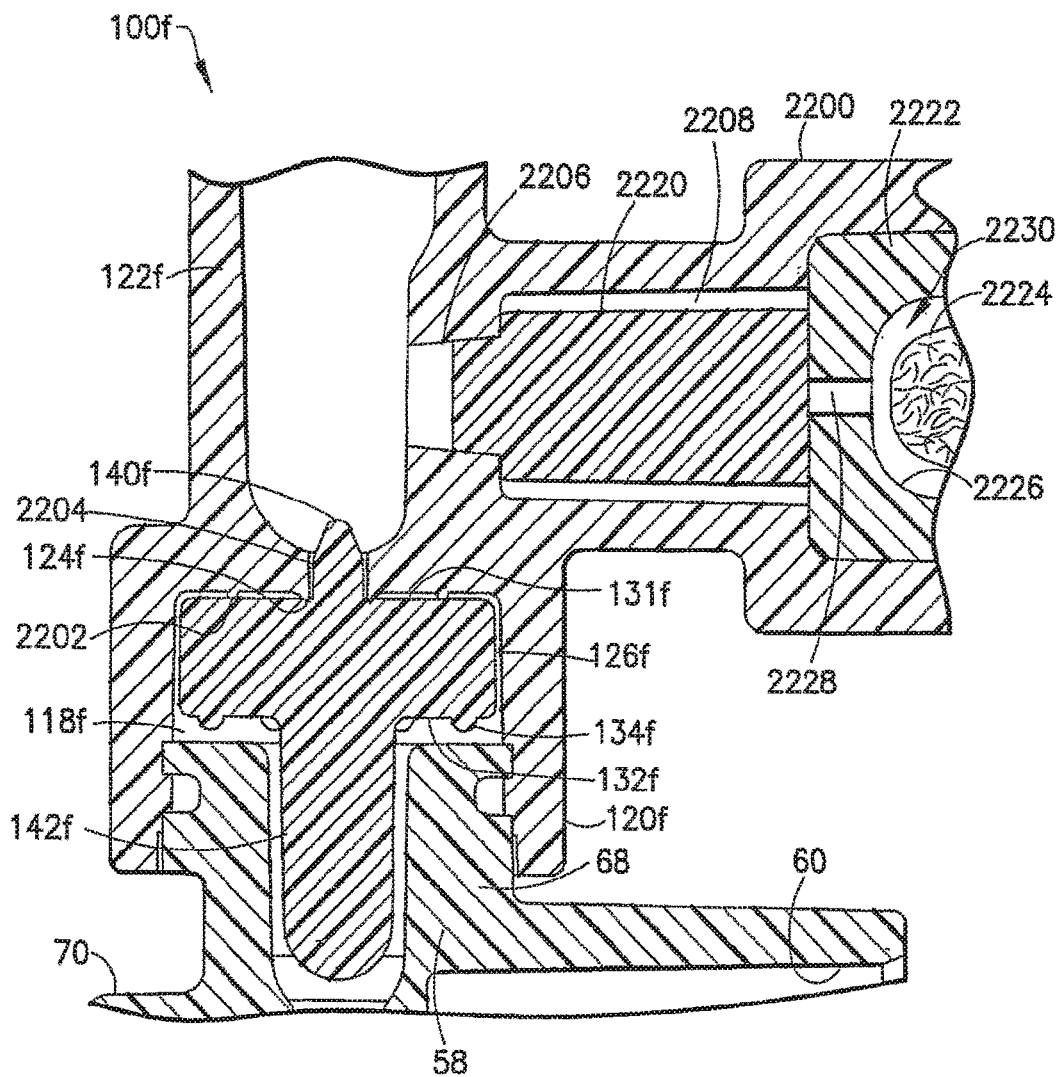
FIG. 28 is a transverse cross-sectional view of a portion of the flow-based pressure isolation mechanism of FIG. 26 illustrating a flow initiating mechanism.

Pressure isolation mechanism 100*f* includes a housing body 102*f* defining an internal chamber or cavity 118*f* therein which, in this embodiment, is in direct fluid communication with and is formed in part by inlet port 120*f* as shown in FIGS. 27-28. Inlet port 120*f* is adapted to engage or mate with pressure transducer port 68 on Y-T fitting 58 via threaded or welded engagement in this embodiment. Accordingly, internal cavity 118*f* is in substantially direct fluid communication with pressure transducer port 68 which allows fluid flow into internal chamber or cavity 118*f* during a fluid injection procedure involving fluid injector 14 and syringe 32. Housing body 102*f* further comprises or defines an isolation port 122*f* similar to that described previously for connection of pressure transducer P and tubing T associated therewith FIG. 2A and a branching flow initiating port 2200 associated with isolation port 122*f*. As is apparent from FIGS. 27-28, isolation port 122*f* is somewhat elongated to allow for connection of branching flow initiating port 2200. Flow initiating port 2200 is in fluid communication with and positioned generally perpendicularly to isolation port 122*f*. Isolation port 122*f* may be formed as a standard luer connector. In the illustrated embodiment, isolation port 122*f* is shown as a female luer for exemplary purposes only and a male luer connection may be provided in place of the female luer if desired. Other connection methods may be used such as a bonded tube connection, customized connection, and the like. The illustration of luer-type fittings should not be considered limiting in this disclosure.

Housing 102*f* defines a primary seal seat or rim 124*f* internally within internal cavity 118*f* that is generally circular (i.e., annular) in configuration but may take other suitable forms. Generally, seal seat 124*f* is a raised continuous lip or rim against which a valve element or structure may make a sealing connection or engagement and performs the same function as in previously discussed embodiments. Seal seat 124*f* is provided in internal cavity 118*f* between inlet port 120*f* and isolation port 122*f*. In addition, a circular sealing rib or secondary seal seat 2202 may also be provided within internal cavity 118*f* and is formed by housing body 102*f* radially outward and concentric to seal seat 124*f*. As will be apparent from FIGS. 27-28, housing 102*f* is a unitary body in this embodiment which defines seal seat 124*f* and secondary or stabilizing seal seat 2202 in opposition to valve member 126*f* described herein. Secondary or stabilizing seal seat 2202 aids seal seat 124*f* in forming a generally leak proof seal between housing 102*f* and valve member 126*f*. Secondary seal seat 2202 is provided to enhance the sealing characteristics of the valve member 126*f* and is optional.

Valve member 126*f* is disposed within internal cavity 118*f* between inlet port 120*f* and isolation port 122*f*. Valve member 126*f* is adapted to engage and seal against seal seat 124*f* and secondary seal seat 2202 but is disposed within the internal cavity 118*f* to be free-floating therein. By free-floating it is generally meant that valve member 126*f* is freely movable within internal cavity 118*f* in response to fluid flow into inlet port 120*f* so that the valve member 126*f* may engage and seal against at least seal seat 124*f* to close-off fluid flow through internal cavity 118*f* thereby isolating isolation port 122*f*. Valve member 126*f* includes a generally unitary disk-shaped body formed of compliant material, such as rubbers, thermoplastic elastomers or silicone. In contrast to previous embodiments, valve member 126*f* is a unitary structure in this embodiment formed of resiliently deformable material (rubbers, thermoplastic elastomers or silicone as examples) and does not include a stiffening component or element but such a stiffening structure may be provided if desired. Valve member 126*f* may be formed with opposing projections 140*f*, 142*f* extending from top and bottom sides 131*f*, 132*f*, respectively, in a generally similar manner to valve member 126*a* discussed previously in connection with FIG. 7. Top projection 140*f* is substantially smaller than bottom projection 142*f* and both projections 140*f*, 142*f* are now provided mainly as centering structures for centering valve member 126*f* in internal cavity or chamber 118*f*. However, in this embodiment top projection 140*f* extends through an aperture 2204 connecting internal cavity or chamber 118*f* with isolation port 122*f* and bottom projection 142*f* is now formed to depend into pressure transducer port 68 in Y-T connector 58 as shown in FIGS. 27-28. Moreover, a series of tab members 134*f* are provided on the bottom side 132*f* of valve member 126*f* in this embodiment and which prevent the valve member 126*f* from collapsing onto pressure transducer port 68 and potentially forming a reverse seal with pressure transducer port 68.

Figure 29:
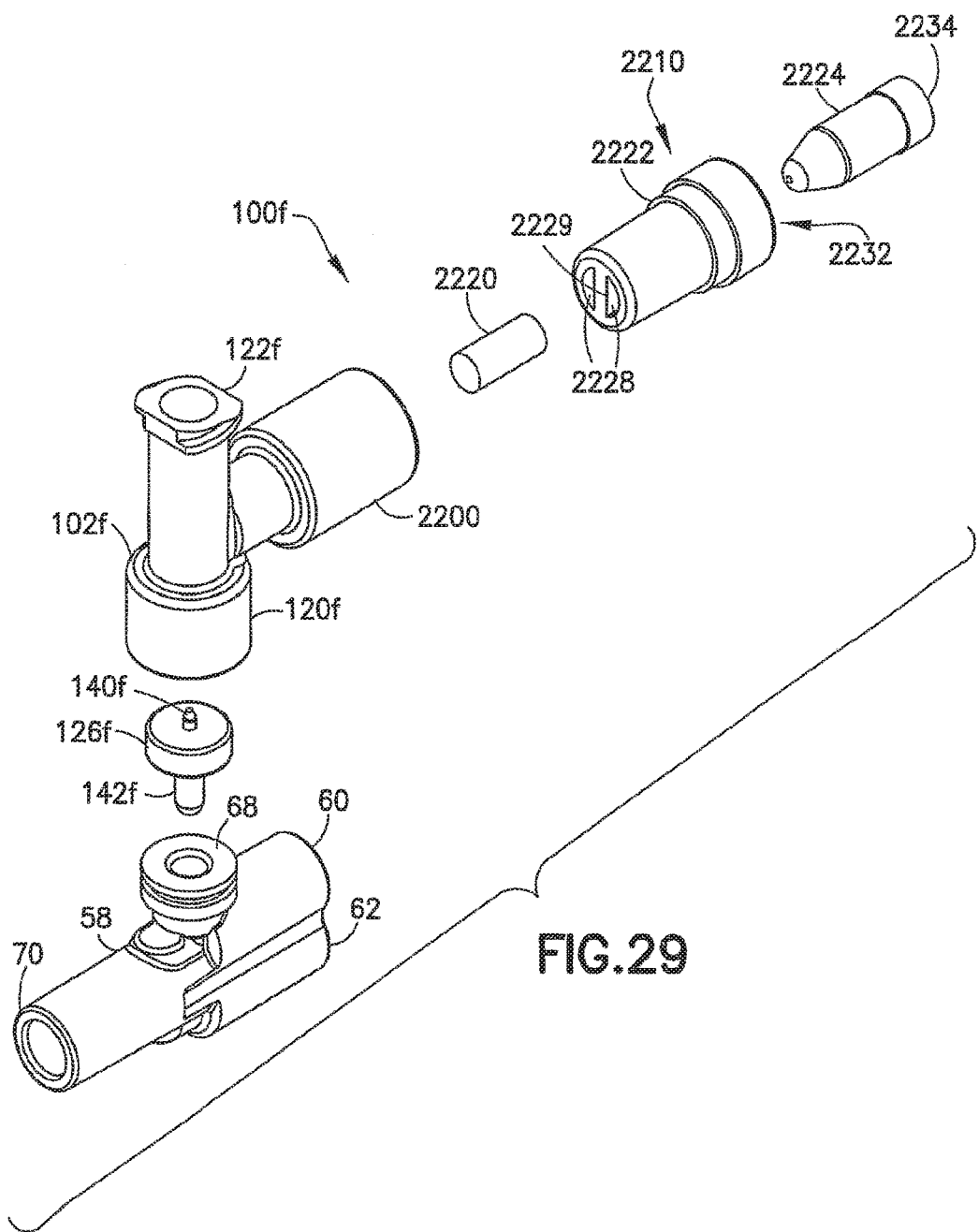
FIG. 29 is an exploded perspective view of the flow-based pressure isolation mechanism of FIG. 26 including the flow initiating mechanism.

Flow initiating port 2200 is connected with isolation port 122*f* via a branch aperture 2206 and defines a branch chamber or lumen 2208 connected to branch aperture 2206. Branch chamber or lumen 2208 is stepped as illustrated in FIGS. 27-28 to accommodate a flow initiating mechanism 2210 therein. Flow initiating mechanism 2210 includes a flow initiating member 2220 and a retainer member 2222; flow initiating member 2220 and retainer member 2222 are disposed, in sequence, in branch chamber or lumen 2208. As illustrated in FIGS. 27-28, housing 102*f* and flow initiating port 2200 are desirably formed as a single, unitary member. Flow initiating member 2220 is held in place within lumen 2208 by hollow retainer member 2222 positioned in the larger stepped portion of branch chamber or lumen 2208. An adhesive, solvent, laser, or ultrasonic weld may be used to maintain retainer member 2222 within branch chamber or lumen 2208. Retainer member 2222 is hollow to receive and support an air inlet prevention filter 2224. In particular, retainer member 2222 defines a hollow area or bore 2226 that accommodates air inlet prevention filter 2224. Bore 2226 is connected via a connecting aperture 2228 to be open to branch chamber or lumen 2208, with flow initiating member 2220 interposed between connecting aperture 2228 and branch aperture 2206. As shown in FIG. 29, connecting aperture 2228 may be bifurcated via a dividing member or segment 2229. Retainer member 2222 may be held in place in branch chamber or lumen 2208 via any suitable joining method with the structure of flow initiating port 2200 such as via adhesive, solvent, laser, or ultrasonic weld methods. As shown in FIGS. 27-28, a certain amount of clearance is provided radially about flow initiating member 2220 and the inner wall of flow initiating port 2200 defining branch chamber or lumen 2208. Likewise, a certain amount of distal clearance 2230 is provided at the distal end of filter 2224 and connecting apertures 2228 to allow fluid flow entering through connecting apertures 2228 to contact the material forming filter 2224. Flow initiating member 2220 may be formed of resiliently deformable material (rubbers, thermoplastic elastomers or silicone as examples) and filter 2224 may be formed of porous materials such as porous polyethylene or porous polypropylene as non-limiting examples.

Fluid initiating member 2220 is generally adapted to initiate a small flow around valve member 126$f$ such that valve member 126$f$ operates to a closed position substantially upon flow initiation. Filter 2224 is configured such that when it is wetted with fluid passing around the body of flow initiating member 2220, it prevents air from entering lumen 2208 if fluid initiating member 2220 is somehow faulty. Additionally, when flow initiating member 2220 functions properly, filter 2224 is adapted to prevent an outward spray of fluid from a proximal end opening 2232 in retainer member 2222. In normal operation, valve member 126$f$ is responsive to fluid flow in inlet port 120$f$ so that the valve member 126$f$ may seat and seal against at least seal seat 124$f$ to form a closed state or condition of pressure isolation mechanism 100$f$, as explained in detail previously in this disclosure. When valve member 126$f$ is not seated against seal seat 124$f$, valve member 126$f$ defines an open state or condition of the pressure isolation mechanism 100$f$ allowing hemodynamic pressure readings to be taken as desired via pressure transducer. Valve member 126$f$ is configured to isolate pressure transducer P and connecting tubing T associated therewith connected to isolation port 122 from over pressure during pressure injections involving fluid injector 14 and syringe 32.

In some instances, such as a low flow situation into internal cavity or chamber 118$f$, insufficient flow may be present to cause valve member 126$f$ to immediately displace to the closed position seated against at least seal seat 124$f$ and typically also against secondary seal seat 2202. Flow initiating member 2220 is adapted to provide sufficient upstream capacitance to allow a small flow of fluid to initiate around valve member 126$f$ such that valve member 126$f$ operates to the closed position substantially upon flow initiation. By sufficient it is generally meant that by virtue of the presence of flow initiating mechanism 2210, enough capacitance is present upstream of valve member 126$f$ to allow flow to initiate around the valve member 126$f$ and thereby operate the valve member 126$f$ to the closed position and vice versa (i.e., return to an open position). Flow initiating member 2220 provides this sufficient upstream capacitance by displacing axially (compresses in an axial direction) in branch lumen 2208 which allows fluid flow to commence about valve member 126$f$, into isolation port 122$f$ and through branch aperture 2206 into branch lumen 2208. This fluid passes around the body of flow initiating member 2220 to enter bore 2226 via connecting apertures 2228. Once fluid enters bore 2226, filter 2224 becomes wetted and saturated with liquid. The presence of filter 2224 prevents a spray of liquid from being ejected from the proximal end opening 2232 in retainer member 2222. Moreover, once wetted and saturated with liquid, the surface tension of the liquid at a proximal end 2234 of filter 2224 prevents air from intruding into bore 2226 and branch lumen 2208 which could potentially be withdrawn into internal cavity or chamber 118$f$ with attendant possibility of being injected inadvertently into a patient.

Figure 30:
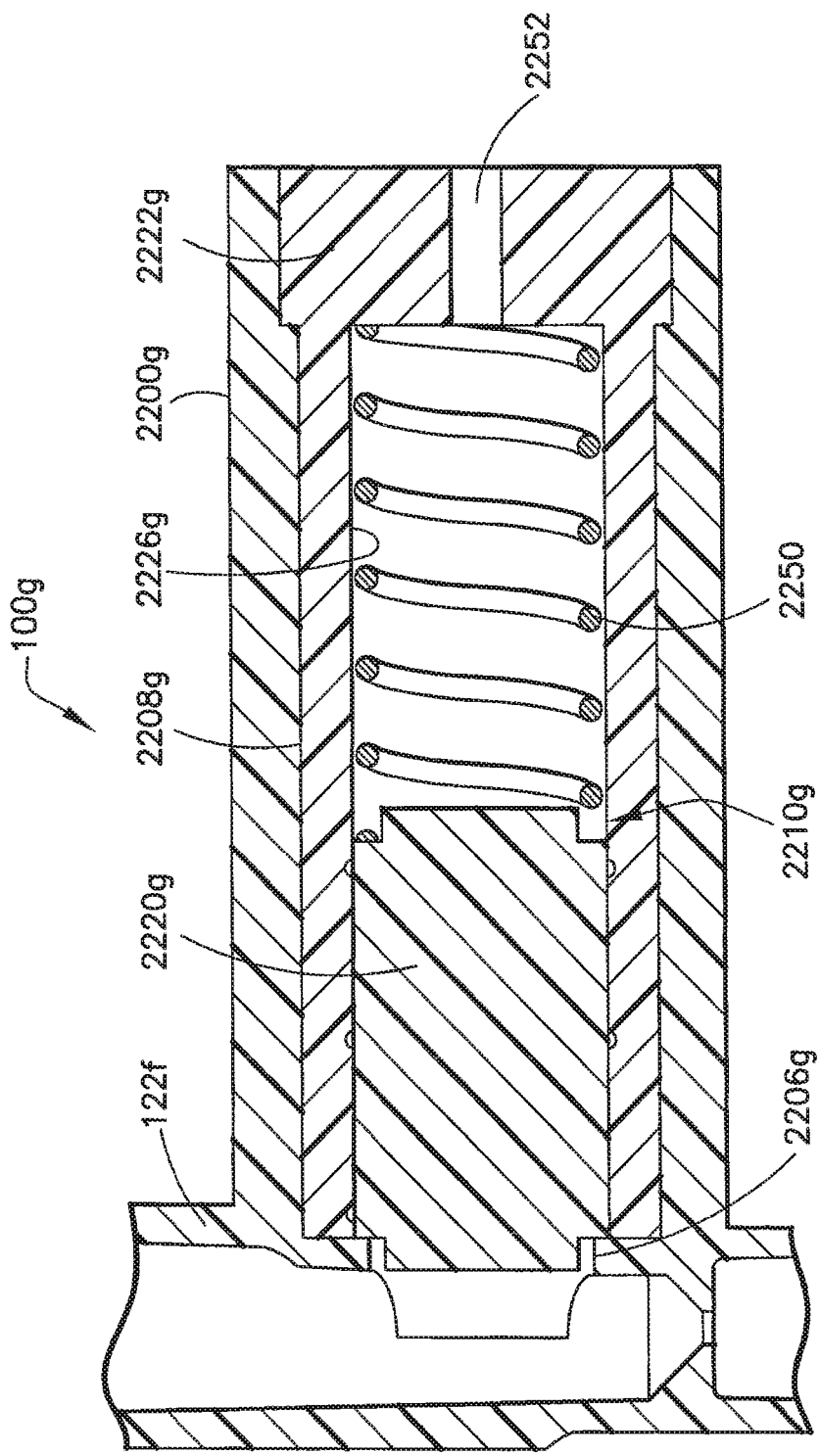
FIG. 30 is a cross-sectional view of a variation of the flow initiating mechanism shown in FIGS. 27-29.

In place of the open structure of flow initiating mechanism 2210 described above, a closed (sealed) type structure could be implemented in accordance with the teachings of this disclosure. As an example shown in FIG. 30, such a closed structure could entail providing flow initiating mechanism 2210$g$ with a biasing spring 2250 which would provide the necessary upstream capacitance in generally the same operational manner discussed previously. In particular, it is envisioned that the biasing spring 2250 would replace filter 2224 and be retained by the retainer member 2222$g$ provided in a slightly different configuration. Biasing spring 2250 acts upon the flow initiating member 2220$g$ to provide the needed capacitance described previously. It will be appreciated that the biasing spring 2250 could be made as a resilient appendage integral to flow initiating member 2220$g$. As FIG. 30 shows, retainer member 2222$g$ is adapted to enclose both the biasing spring 2250 and flow initiating member 2220$g$ and may be maintained in flow initiating port 2200 by any of the joining methods described previously in this disclosure. A vent opening 2252 is provided for venting bore 2226$g$.

While several embodiments of a flow-based pressure isolation mechanism and fluid delivery system including flow-based pressure isolation techniques and methods associated therewith were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A method of protecting a pressure transducer from fluid pressure damage using a pressure isolation mechanism comprising an inlet port, an isolation port, and an internal cavity wherein a free floating, fluid flow responsive valve member is disposed and adapted to engage a seal seat in the internal cavity, and a flow initiating mechanism is associated with the isolation port, the method comprising:
   associating the pressure transducer with the isolation port;
   placing a pressurizing device for delivering fluid under pressure in fluid connection with the inlet port;
   actuating the pressurizing device to cause fluid flow in the inlet port such that the free floating, fluid flow responsive valve member engages the seal seat to attain a closed position, to prevent fluid flow between the inlet port and the isolation port, and to prevent overpressure in the isolation port; and
   reading hemodynamic pressure signals with the pressure transducer transmitted at least in part through a body of the valve member or a portion thereof in the closed position,
   wherein upon actuation of the pressurizing device, the flow initiating mechanism initiates flow around the valve member such that the valve member operates to the closed position upon fluid flow initiation.

2. The method of claim 1, further comprising deactivating the pressurizing device and allowing the valve member to attain an open position disengaged from the seal seat permitting fluid communication between the inlet port and the isolation port.

3. The method of claim 2, further comprising reading hemodynamic pressure signals with the pressure transducer transmitted via the fluid communication between the inlet port and the isolation port in the open position of the valve member.

4. The method of claim 1, wherein the body of the valve member or a portion thereof comprises a compliant material.

5. The method of claim 4, wherein the compliant material is selected to transmit hemodynamic pressure signals through the valve member to the pressure transducer associated with the isolation port.

6. The method of claim 2, wherein the valve member attains the open position by a reverse fluid flow generated in the isolation port.

7. The method of claim 1, wherein the inlet port is placed in fluid communication with the pressurizing device by using a fitting to connect the inlet port to the pressurizing device.

8. The method of claim 7, wherein the fitting comprises a Y-T fitting.

9. A method of protecting a pressure transducer from fluid pressure damage using a pressure isolation mechanism comprising an inlet port, an isolation port, and an internal cavity wherein a free floating, fluid flow responsive valve member is disposed and adapted to engage a seal seat in the internal cavity, and a flow initiating mechanism comprising a flow initiating member is associated with the isolation port, the method comprising:
  associating the pressure transducer with the isolation port;
  placing a pressurizing device for delivering fluid under pressure in fluid connection with the inlet port;
  actuating the pressurizing device to cause fluid flow in the inlet port such that the free floating, fluid flow responsive valve member engages the seal seat to attain a closed position, to prevent fluid flow between the inlet port and the isolation port, and to prevent overpressure in the isolation port; and
  reading hemodynamic pressure signals with the pressure transducer transmitted at least in part through a body of the valve member or a portion thereof in the closed position,
  wherein the flow initiating member provides upstream volume capacitance to initiate fluid flow around the valve member such that the valve member operates to the closed position upon fluid flow initiation and operates to an open position upon fluid flow cessation.

10. The method of claim 9, further comprising deactuating the pressurizing device and allowing the upstream capacitance to act upon the valve member to attain the open position disengaged from the seal seat and permitting fluid communication between the inlet port and the isolation port.

11. The method of claim 10, further comprising reading hemodynamic pressure signals with the pressure transducer transmitted via the fluid communication between the inlet port and the isolation port in the open position of the valve member.

12. The method of claim 9, wherein the body of the valve member or a portion thereof comprises a compliant material.

13. The method of claim 12, wherein the compliant material is selected to transmit hemodynamic pressure signals through the valve member to the pressure transducer associated with the isolation port.

14. The method of claim 9, wherein the valve member attains the open position by a reverse fluid flow generated in the isolation port caused by the upstream capacitance.

15. The method of claim 9, wherein the inlet port is placed in fluid communication with the pressurizing device by using a fitting to connect the inlet port to the pressurizing device.

16. The method of claim 15, wherein the fitting comprises a Y-T fitting.

17. The method of claim 9, the pressure isolation mechanism further comprising an air inlet prevention filter disposed in a retainer retaining the flow initiating mechanism in fluid communication with the isolation port, the air inlet prevention filter adapted to prevent air from entering the internal cavity when the filter is wetted, the method further comprising:
  wetting the air inlet prevention filter with fluid.

18. The method of claim 9, wherein the actuating of the pressurizing device causes the flow initiating member to compress axially to store the upstream volume capacitance.

* * * * *

UNITED STATES PATENT AND TRADEMARK OFFICE
CERTIFICATE OF CORRECTION

PATENT NO. : 10,137,294 B2  
APPLICATION NO. : 15/385153  
DATED : November 27, 2018  
INVENTOR(S) : Spohn et al.

Page 1 of 1

It is certified that error appears in the above-identified patent and that said Letters Patent is hereby corrected as shown below:

In the Specification
In Column 22, Line 55, delete "saline delivery system" and insert -- fluid delivery system --, therefor.
In Column 22, Line 58, delete "pressure saline fluid" and insert -- pressure fluid --, therefor.
In Column 26, Line 38, delete "Y-T connector" and insert -- Y-T fitting --, therefor.
In Column 27, Line 19, delete "Fluid initiating member" and insert -- flow initiating member --, therefor.
In Column 27, Line 25, delete "fluid initiating member" and insert -- flow initiating member --, therefor.

Signed and Sealed this
Fifth Day of March, 2019

Andrei Iancu
*Director of the United States Patent and Trademark Office*